(12) United States Patent
Neustadter

(10) Patent No.: US 11,464,638 B2
(45) Date of Patent: Oct. 11, 2022

(54) ADJUSTABLE SELF-LOCKING PAPILLARY MUSCLE BAND

(71) Applicant: Cardiac Success Ltd., Yokneam (IL)

(72) Inventor: David Neustadter, Nof Ayalon (IL)

(73) Assignee: Cardiac Success Ltd, Yokneam (IL)

( * ) Notice: Subject to any disclaimer, the term of this patent is extended or adjusted under 35 U.S.C. 154(b) by 0 days.

(21) Appl. No.: 17/657,440

(22) Filed: Mar. 31, 2022

(65) Prior Publication Data

US 2022/0218484 A1 Jul. 14, 2022

Related U.S. Application Data

(63) Continuation-in-part of application No. 16/780,520, filed on Feb. 3, 2020, now Pat. No. 11,318,019, which is a continuation-in-part of application No. 16/166,291, filed on Oct. 22, 2018, now Pat. No. 10,548,732.

(60) Provisional application No. 62/575,538, filed on Oct. 23, 2017.

(51) Int. Cl.
*A61F 2/24* (2006.01)

(52) U.S. Cl.
CPC .......... *A61F 2/2487* (2013.01); *A61F 2/2457* (2013.01); *A61F 2/2466* (2013.01); *A61F 2/2481* (2013.01); *A61F 2220/0016* (2013.01); *A61F 2220/0025* (2013.01); *A61F 2220/0033* (2013.01); *A61F 2230/0065* (2013.01); *A61F 2250/0007* (2013.01); *A61F 2250/0012* (2013.01)

(58) Field of Classification Search
CPC .... A61F 2/2442; A61F 2/2445; A61F 2/2448; A61F 2/2451; A61F 2/2457; A61F 2/2466; A61F 2/2478; A61F 2/2487
See application file for complete search history.

(56) References Cited

U.S. PATENT DOCUMENTS

| | | | |
|---|---|---|---|
| 6,629,534 B1 | 10/2003 | St. Goar | |
| 7,331,972 B1 | 2/2008 | Cox | |
| 9,125,742 B2 | 9/2015 | Yoganathan et al. | |
| 9,867,702 B2 | 1/2018 | Keränen et al. | |
| 9,877,833 B1 | 1/2018 | Bishop | |

(Continued)

OTHER PUBLICATIONS

International Application No. PCT/iB18/01370, date Oct. 22, 2018.

(Continued)

*Primary Examiner* — Suba Ganesan
(74) *Attorney, Agent, or Firm* — Finnegan, Henderson, Farabow, Garrett & Dunner, LLP

(57) ABSTRACT

Embodiments of the present disclosure include a cardiac device comprising a band configured to form a loop within a heart and including a first end and a second end, a plurality of sequential locking segments located in a region of the band near the second end, and an actuatable clasp located at or near the first end. Each locking segment may have a ledged region and a ramped region. The actuatable clasp may be configured to form a fixed length loop by locking onto the ledged region of a locking segment after the second end has been inserted into the clasp. Adjacent locking segments may be configured to flex relative to each other, thereby enabling adjacent ramped regions to cooperate with each other to facilitate a sliding of the segments into the clasp.

20 Claims, 26 Drawing Sheets

(56) References Cited

U.S. PATENT DOCUMENTS

| | | |
|---|---|---|
| 9,937,044 B2 | 4/2018 | Sutherland |
| 10,010,419 B2 | 7/2018 | Yoganathan et al. |
| 10,058,428 B1 | 8/2018 | Neustadter |
| 10,195,031 B2 | 2/2019 | Nasr |
| 2005/0197696 A1 | 9/2005 | Duran |
| 2006/0229708 A1 | 10/2006 | Powell |
| 2007/0051377 A1 | 3/2007 | Douk et al. |
| 2007/0100439 A1 | 5/2007 | Cangialosi |
| 2007/0255396 A1 | 11/2007 | Douk |
| 2009/0009941 A1 | 1/2009 | De Marchena |
| 2009/0082619 A1 | 3/2009 | De Marchena |
| 2009/0149872 A1* | 6/2009 | Gross ............... A61F 2/2466 606/139 |
| 2009/0234318 A1 | 9/2009 | Loulmet |
| 2010/0121437 A1 | 5/2010 | Subramanian |
| 2010/0185278 A1 | 7/2010 | Schankereli |
| 2010/0210899 A1 | 8/2010 | Schankereli |
| 2011/0015476 A1 | 1/2011 | Franco |
| 2011/0060407 A1 | 3/2011 | Ketai |
| 2011/0166649 A1 | 7/2011 | Gross |
| 2012/0123531 A1 | 5/2012 | Tsukashima |
| 2014/0379006 A1 | 12/2014 | Sutherland |
| 2015/0127093 A1 | 5/2015 | Hosmer et al. |
| 2016/0262879 A1 | 9/2016 | Meiri et al. |
| 2017/0119368 A1 | 5/2017 | Solem |
| 2017/0135818 A1 | 5/2017 | Axelrod |
| 2017/0156861 A1 | 6/2017 | Longoria |
| 2017/0181851 A1 | 6/2017 | Annest |
| 2018/0296340 A1 | 10/2018 | Yoganathan et al. |
| 2018/0311043 A1 | 11/2018 | Neustadter |
| 2019/0117399 A1 | 4/2019 | Neustadter |
| 2019/0358037 A1 | 11/2019 | McAfee et al. |
| 2019/0380699 A1 | 12/2019 | Bad-Boychuk et al. |
| 2021/0161667 A1 | 6/2021 | Hou et al. |

OTHER PUBLICATIONS

International Search Report and Written Opinion issued by the International Searching Authority for PCT International Patent Application No. PCT/IB2018/001370, dated May 31, 2019 (12 pgs.).

* cited by examiner

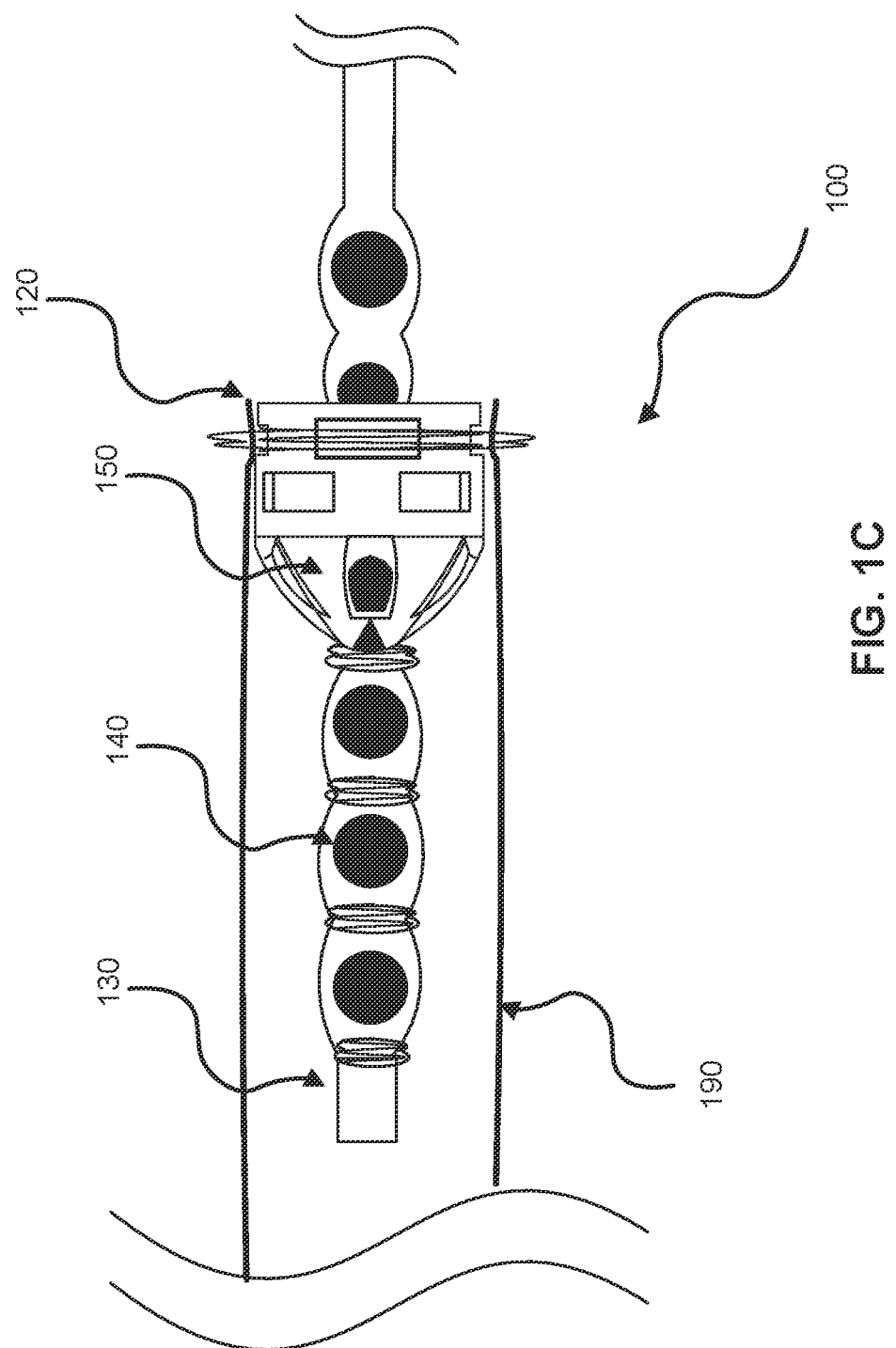

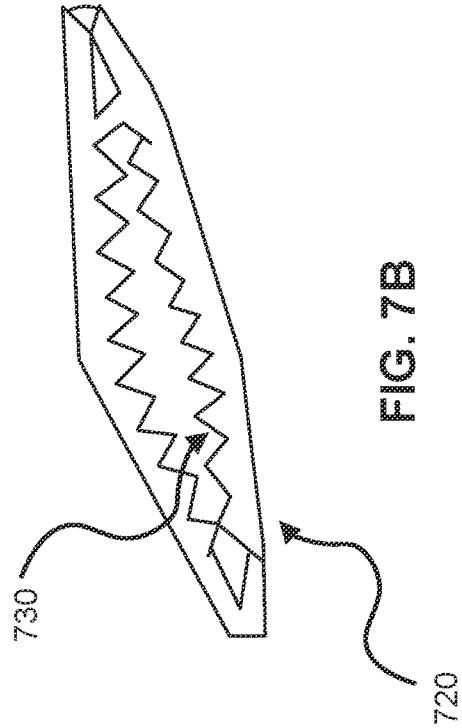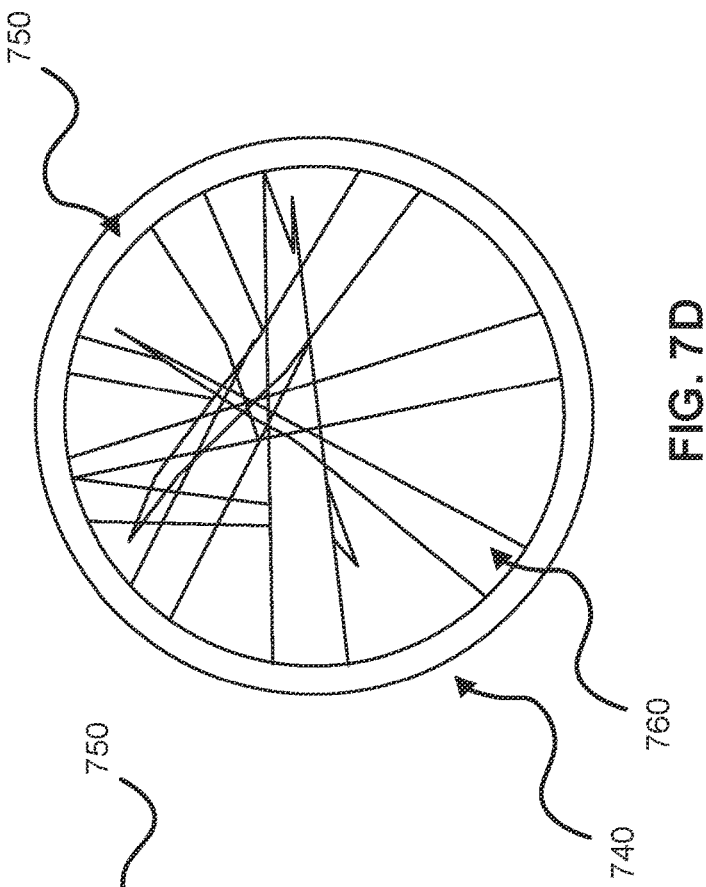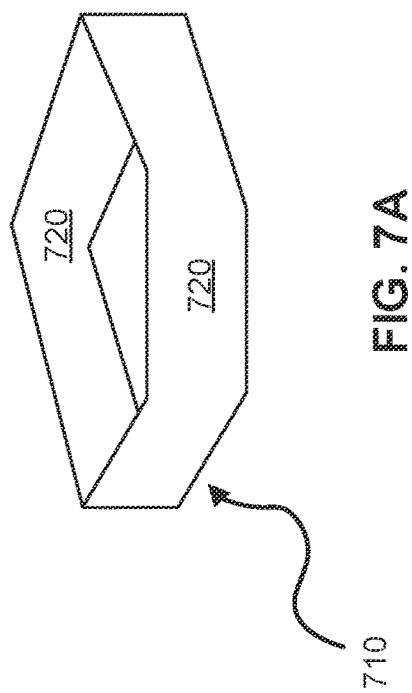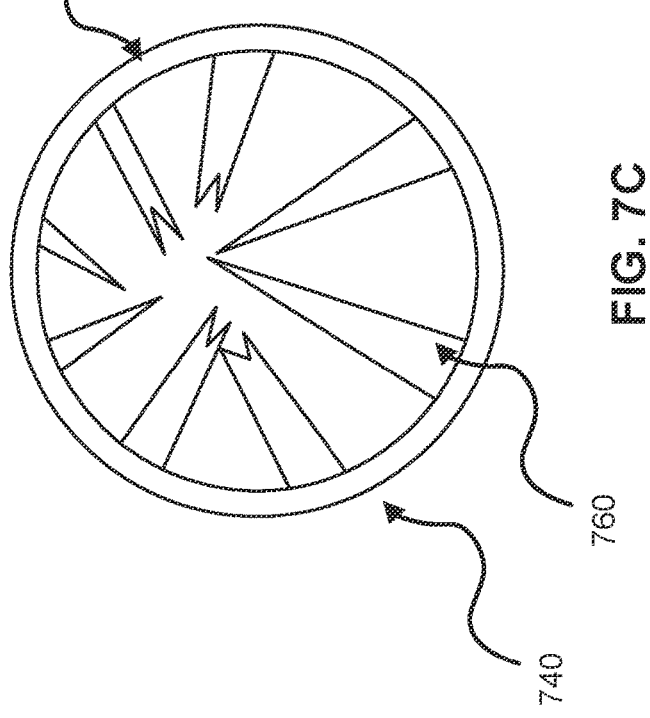

ADJUSTABLE SELF-LOCKING PAPILLARY MUSCLE BAND

CROSS-REFERENCE TO RELATED APPLICATIONS

This application is a continuation of U.S. Non-Provisional patent application Ser. No. 16/780,520, filed Feb. 3, 2020 (now allowed), which is a continuation-in-part of U.S. Non-Provisional patent application Ser. No. 16/166,291, filed Oct. 22, 2018 (now U.S. Pat. No. 10,548,732), which claims priority from U.S. Provisional Patent Application No. 62/575,538, filed Oct. 23, 2017. The disclosures of the above-identified applications are expressly incorporated herein by reference in their entireties.

FIELD OF THE INVENTION

Some applications of the present invention relate in general to devices and methods for improving cardiac function. More specifically, some applications of the present invention relate to a cardiac device for transcatheterly repositioning papillary muscles in a heart of a body.

BACKGROUND

Repositioning the papillary muscles within the ventricles of the heart during atrioventricular valve repair surgery may improve outcomes. The displacement of the papillary muscles, due to ischemia, heart failure, or other causes of ventricular reshaping, may result in tethering of the valve leaflets, which may interfere with their normal functioning. Repairs that focus only on the valve annulus often result in recurrence of regurgitation due to leaflet tethering.

Methods of papillary muscle repositioning include sutures from the papillary muscle(s) up to the annulus of the valve or the aorta, slings that encircle multiple papillary muscles to pull the papillary muscles together, and sutures to pull the papillary muscles together. However, these methods of papillary muscle repositioning are typically performed during an open-heart surgery.

Another method of repositioning papillary muscles include positioning a band around the papillary muscles to improve cardiac function. For example, a transcatheter papillary muscle band is inserted into the ventricle via a catheter and locked tightly around the base of the papillary muscles to reposition the papillary muscles and improve cardiac function. Some transcatheter papillary muscle bands include a clasp, which can be actuated via a catheter to lock the band into a loop forming a sling. The clasp may lock onto any one of a number of ridges or ledges along the band, thereby allowing adjustability of the size of the loop before locking the clasp.

In some sling designs, the distal end of the band containing the ridges may be pulled through the clasp until a desired loop size is achieved. Then, the clasp may be actuated to lock onto the ridge of the band that lies within the clasp. Because the band is wrapped tightly around the papillary muscles, during insertion, the distal end of the band may not be inserted into the clasp in a straight configuration, but rather may be inserted at an angle. Due to the angle at which the band is inserted into the clasp, which may be often up to or greater than 90 degrees, the locking ridges in the distal portion of the band may interfere with insertion of the band into the clasp. For example, the ridges may increase the amount of force necessary to pull the band into the clasp and may make the insertion jerky and difficult to control. This interference with insertion into the clasp as a result of the ledges in the band is referred to as the "ledge effect." While a change in the radius of the band is the mechanical feature that allows the clasp to lock onto the ridges, the change in the radius is also the mechanical feature that interferes with smooth insertion of the band into the clasp.

Therefore, a need exists for systems and methods for performing papillary muscle repositioning that is capable of reducing the ledge effect that interferes with smooth insertion of the band into the clasp.

SUMMARY

Presently disclosed embodiments recognize that a need exists for improved devices and methods for repositioning papillary muscles, which can be more easily positioned, adjusted, and locked in place than conventional devices and methods while also reducing the ledge effect. Additionally, presently disclosed embodiments may address the need for devices and methods of repositioning papillary muscles that has the potential to enable papillary muscle repositioning to be performed on a pumping heart via a catheter. Moreover, conventional devices and methods for papillary muscle repositioning have had little commercial success. There is therefore a need for improved devices and methods, regardless of whether delivered via a catheter or in some other way.

The embodiments of the present disclosure include devices and methods of repositioning papillary muscles. Advantageously, the exemplary embodiments provide a method of repositioning papillary muscles by delivering a band through a trabeculae. The band may comprise a plurality of sequential locking segments to be inserted into an adjustable clasp to form a loop. Various embodiments of the disclosure may include one or more of the following aspects.

In accordance with an embodiment of the present disclosure, a cardiac device is provided, comprising a band configured to form a loop within a heart and including a first end and a second end, and a plurality of sequential locking segments located in a region of the band near the second end. Each locking segment may include a ledged region and a ramped region. The cardiac device may also comprise an adjustable clasp located at or near the first end. The adjustable clasp may be configured to form a fixed length loop by locking onto the ledged region of a locking segment after the second end has been inserted into the clasp. The adjacent locking segments may be configured to flex relative to each other, thereby enabling adjacent ramped regions to cooperate with each other to facilitate a sliding of the segments into the clasp.

According to an embodiment of the present disclosure, at least a portion of the band may be a tube, and the plurality of sequential locking segments may be located inside the tube. According to another embodiment of the present disclosure, each of the locking segments may be cone-shaped. In some embodiments, the adjacent locking segments may be linked together by a mechanical joint configured to allow the locking segments to rotate relative to each other in at least one plane. In yet another embodiment, the adjacent locking segments may include beads strung on a flexible wire. In some embodiments, the locking segments may be separated by spacer beads. In some embodiments, at least a portion of each spacer bead may be located inside a hollowed interior of a locking segment.

According to another embodiment of the present disclosure, the adjacent locking segments may include a hollowed interior such that the ramped region of each locking segment can rotate relative to a centerline of a chain of sequential locking segments to reduce a magnitude of a ledge between adjacent locking segments. In some embodiments, the plurality of sequential locking segments may be integrally formed of a single piece, and the single piece may include regions connecting the plurality of sequential locking segments. The regions may be more flexible than the locking segments.

In yet another embodiment of the present disclosure, the ledged region and the ramped region of the plurality of sequential locking segments may be ramped and ridged in only one plane such that the ledged region and the ramped region have at least one side that is smooth with no ledges.

According to another embodiment of the present disclosure, the band may be made of a material configured to allow the adjustable clasp to close on an outside surface of the tube and lock firmly on the ledged region of the locking segment inside the tube. In some embodiments, the band may include at least one of polytetrafluoroethylene (PTFE), expanded polytetrafluoroethylene (ePTFE), or Dacron.

According to another embodiment of the present disclosure, the plurality of sequential locking segments may include a first end and a second end. The second end of the band may be connected to the first end of the plurality of sequential locking segments. In some embodiments, the second end of the plurality of sequential locking segments may be connected to a location along the band.

According to another embodiment of the present disclosure, the locking segments may include an indentation, and the indentation may be configured such that, when the band is flexed, adjacent locking segments are configured to align with each other such that there is no ledge between the adjacent locking segments, thereby providing a smooth surface along an inner surface of the band.

In another embodiment of the present disclosure, the locking segments and the spacer beads may be configured such that, when the band is flexed, adjacent locking segments are configured to align with each other such that there is no ledge between the adjacent locking segments, thereby providing a smooth surface along an inner surface of the band.

In yet another embodiment of the present disclosure, the regions connecting the plurality of sequential locking segments and the locking segments may be configured such that, when the band is flexed, adjacent locking segments are configured to align with each other such that there is no ledge between the adjacent locking segments, thereby providing a smooth surface along an inner surface of the band.

Additional objects and advantages of the embodiments will be set forth in part in the description that follows, and in part will be obvious from the description or may be learned by practice of the embodiments. The objects and advantages of the embodiments will be realized and attained by means of the elements and combinations particularly pointed out in the appended claims.

It is to be understood that both the foregoing general description and the following detailed description are exemplary and explanatory only and are not restrictive of the claims.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1C illustrates a zoomed-in view of the exemplary device of FIG. 1B.

FIG. 7A illustrates an exemplary embodiment of an adjustable clasp, in accordance with an embodiment of the present disclosure;

FIG. 7B illustrates another exemplary embodiment of an adjustable clasp, in accordance with an embodiment of the present disclosure;

FIG. 7C illustrates another exemplary embodiment of an adjustable clasp, in accordance with an embodiment of the present disclosure;

FIG. 7D illustrates another exemplary embodiment of an adjustable clasp, in accordance with an embodiment of the present disclosure;

DETAILED DESCRIPTION OF EMBODIMENTS

The present disclosure relates to methods and devices for improving cardiac function. While the present disclosure provides examples of repositioning papillary muscles by looping a band around the plurality of papillary muscles, it should be noted that aspects of the disclosure in their broadest sense, are not limited to looping a band around the plurality of papillary muscles. Rather, it is contemplated that the forgoing principles may be applied to other devices for improving cardiac function as well. In addition, the looping may also occur through the plurality of spaces among the trabeculae to thereby pull the plurality of papillary muscles closer to each other and reposition the papillary muscles. The plurality of spaces among the trabeculae may be located along the walls of the ventricle of the heart. Accordingly, looping the band through the plurality of spaces among the trabeculae and tightening the band in a single loop may pull the walls of the ventricle of the heart inwards, thereby repositioning the papillary muscles and pulling the papillary muscles closer to each other.

Figure 3:
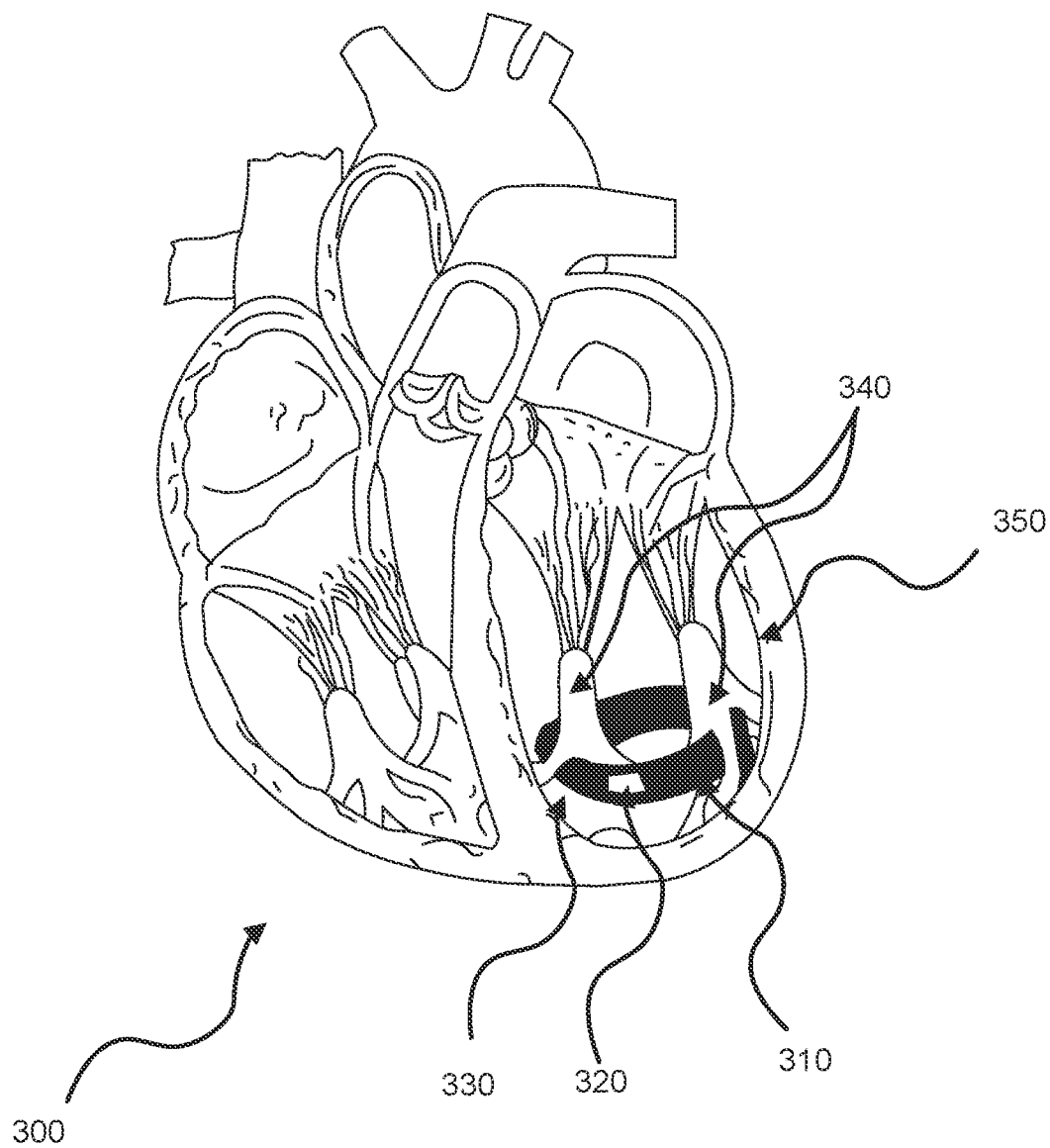
FIG. 3 illustrates an exemplary anatomy of a human heart in which embodiments of the present disclosure may be employed.

The term band refers generally to any element that is capable of either partially or completely encircling a desired anatomy. For example, a band may be an element that is capable of partially or completely encircling a plurality of papillary muscles in the ventricle of the heart in order to bring the papillary muscles closer to each other. A band that loops around the plurality of papillary muscles, as illustrated in FIG. 3, is one example of a device for repositioning papillary muscles, in accordance with the present disclosure. Looping may involve partially or completely surrounding one or more papillary muscles. As discussed above, looping may additionally or alternatively involve passing the band through the plurality of spaces among the trabeculae. In addition, the terms "ridges" and "ledges" refer generally to any projection from a surface of a band, onto which a clasp can lock to form a loop. Accordingly, the terms "ridges" and "ledges" may be used interchangeably.

Figure 1A:
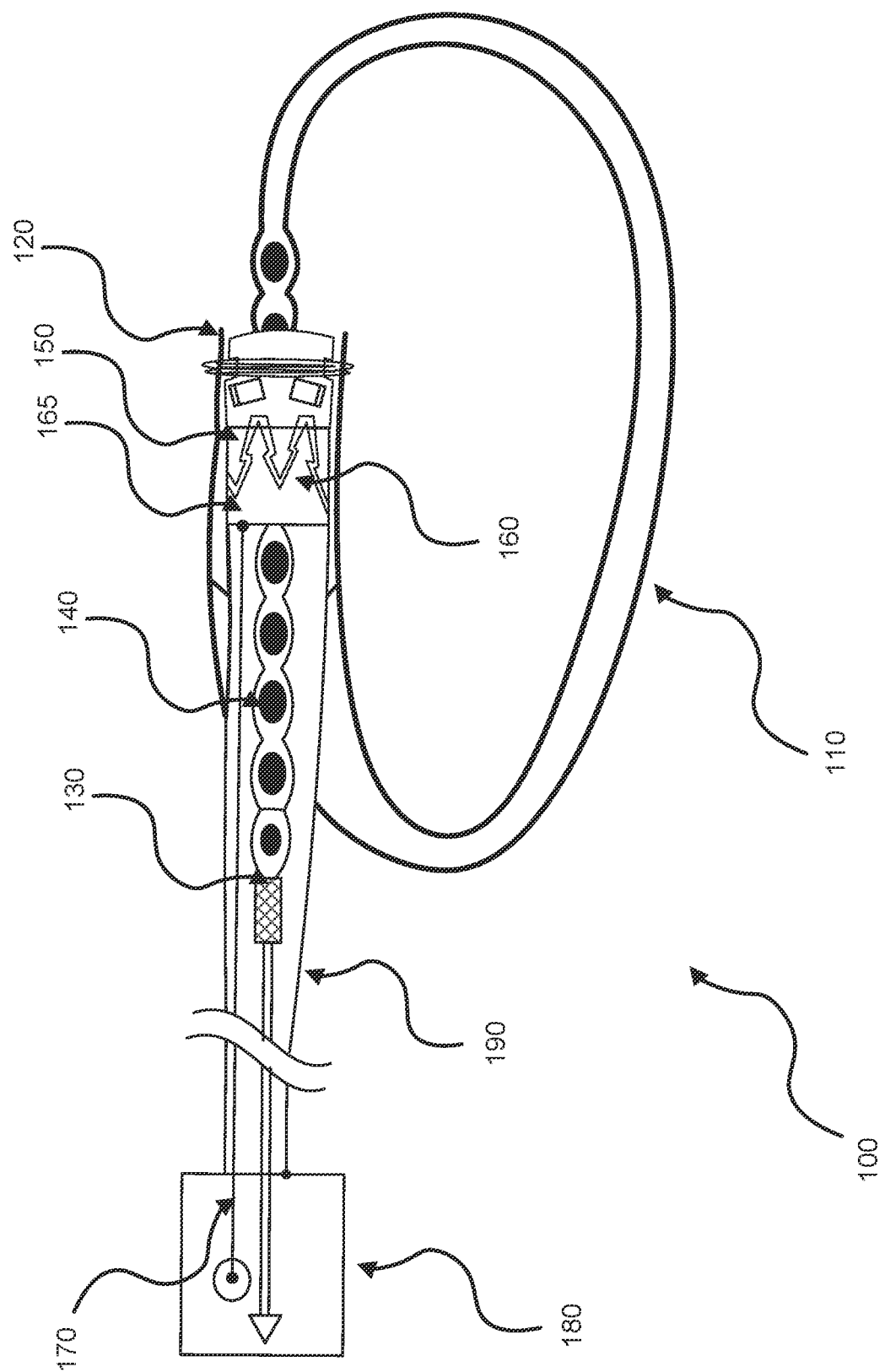
FIG. 1A illustrates an exemplary device for repositioning papillary muscles, in accordance with an embodiment of the present disclosure.
Figure 1B:
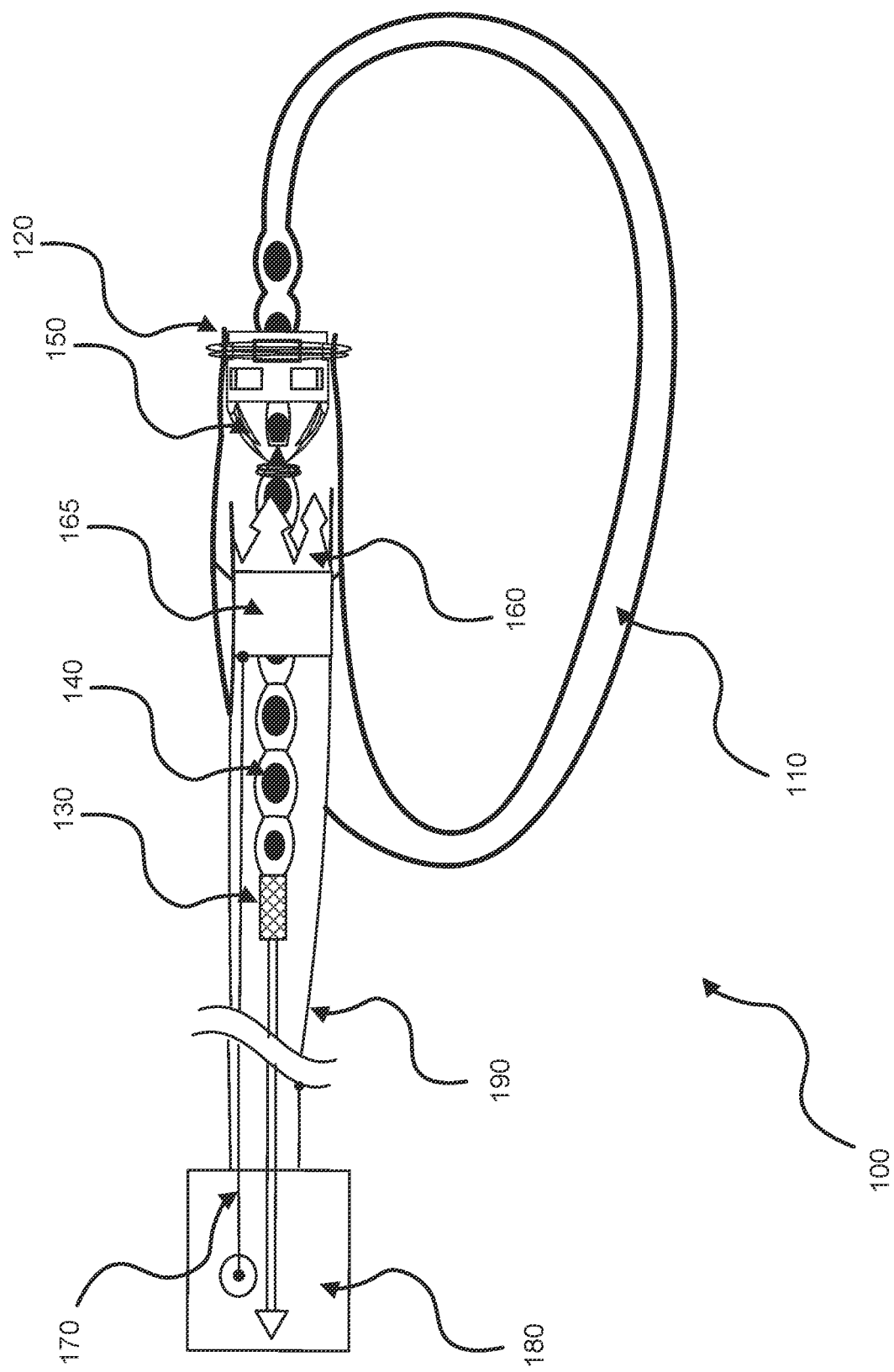
FIG. 1B illustrates an exemplary device for repositioning papillary muscles, in accordance with another embodiment of the present disclosure.

Referring to FIGS. 1A-1C, an exemplary device 100 for repositioning papillary muscles, in accordance with the present disclosure, may include a band 110. The band 110 may comprise a first end 120 and a second end 130. The band 110 may be placed around at least one, optionally at least two, papillary muscles within a ventricle of a heart. The band 110 may be selectively configurable between an elongated configuration, in which the first end 120 is disconnected from the second end 130, and a looped configuration, in which the band 110 is formed into a loop, as illustrated in FIGS. 1A-1C. In some embodiments, the band may be sized to simultaneously encircle a plurality of papillary muscles, thereby forming a loop around the papillary muscles, and pulling the papillary muscles toward each other. The term "band" may include a tube. Alternatively, the band 110 may be a tube. In some embodiments, a portion of the band 110 may be a tube and another portion of the band 110 may not be a tube. The band 110 may have different widths along different portions of its length as illustrated in FIGS. 1A-1C.

In some embodiments of the present disclosure, the band 110 may be made of polytetrafluoroethylene (PTFE), expanded polytetrafluoroethylene (ePTFE), Dacron, and/or any other biologically inert synthetic material with appropriate tensile strength for use in pulling the papillary muscles closer together. In other embodiments, the band 110 may be manufactured by extrusion, knitting, weaving, braiding, or any other method of forming a biologically inert synthetic material into a band or a tubular band. The band 110 may be elastic, non-elastic, partially elastic, or any combination thereof. For example, a portion of the band 110 may be elastic while another portion of the band 110 may be non-elastic. In some embodiments, the band 110 may be made of more than one material. For example, a portion of the band 110 may be made of one material while another portion of the band 110 may be made of a different material. Alternatively, the band 110 may be made of a biological material from the patient, from another human donor, or from animal-derived material.

At or proximate the first end 120 of the band 110, at least one fastener, such as a clasp 150, may be provided. Clasp 150, for example, may be formed of a cut nitinol tube in the form of a crown. Additionally or alternatively, clasp 150 may be formed in the form of a cylinder with multiple flaps protruding from one end. Clasp 150 may be configured to transition from an open configuration (an example of which is illustrated in FIG. 1A) to a closed configuration (an example of which is illustrated in FIGS. 1B and 1C), and vice versa. In the closed configuration, as illustrated in FIG. 1B, the flaps of the clasp 150 may be bent inwards towards the center of the cylinder to form a clasp that grasps a portion of the band 110 that passes through the clasp 150. The flaps may be sharp at the tip to firmly hold and/or puncture the material of the band 110 in the closed configuration. Alternatively, the flaps may be flat or rounded at the tip in order to close between one or more protrusions on the band 110 and prevent a protrusion from passing through the clasp 150. In the open configuration, as illustrated in FIG. 1A, the flaps may be straight with the wall of the cylinder and allow the band 110 to pass through the clasp 150. The flaps may be biased towards the closed configuration and may be elastically bent into the open configuration during positioning and adjustment of the band 110. The flaps may be allowed to return to the closed configuration upon actuation by a clasp actuator (not shown).

As illustrated by way of example in FIGS. 1A-1C, clasp 150 may be attached to the first end 120 of the band 110. In some embodiments, band 110 may be a tube. Accordingly, clasp 150 may be located inside the first end 120 of the band 110. Clasp 150 may comprise one or more cuts in the wall of the tube. A wire or ring may be wrapped around the outside of the band 110 over the one or more cuts in the tube, thereby pushing the material of the band 110 into the cuts in the tube. The foregoing feature may permanently or semi-permanently connect the band 110 to the clasp 150.

The second end 130 of the band 110 may further comprise protruding elements 140 (also called "graspable elements") between which the clasp 150 may close. The protruding elements 140 may be objects, soft or hard balls made of plastic, metal, and/or polymer, protrusions, spikes, or any material that is capable of being grasped by a clasp. In some embodiments, as illustrated in FIGS. 1B and 1C, the protruding elements 140 cannot pass backwards through the closed clasp 150. In some embodiments, the protruding elements 140 may comprise hard balls located inside the band 110, the band 110 being a tube. The band 110 may be pinched between the hard balls by a ring, wire, or string around the outside of the band 110, such that the hard balls cannot move within the band 110. Any number of protrusions can be made at the second end 130 of the band 110, and the clasp 150 may lock closed between any of the protruding elements 140 or past the last protruding element 140, thereby locking at any one of a number of locations along the band 110.

In some embodiments of the present disclosure, the clasp 150 may connect to a distal end 160 of a delivery device 190 such that when the clasp 150 is actuated, the clasp 150 is automatically disconnected from the delivery device 190. An inner and outer diameter of the distal end 160 of the delivery device 190 may be similar to the inner and outer diameter of the clasp 150. In addition, the distal end 160 of the delivery device 190 may be cut with a cut pattern that is complementary to the shape of the flaps of the clasp 150 such that when the clasp 150 is in the open configuration with the flaps bent into the cylindrical shape of the tube, the flaps of the clasp 150 may lock into the cut pattern of the distal end 160 of the delivery device 190, as illustrated in FIG. 1A. When the clasp 150 is allowed to return to the closed configuration, the flaps may bend inwards, thereby disconnecting from the cut pattern at the distal end 160 of the delivery device 190. Accordingly, the clasp 150 and the band 110 may disconnect from the delivery device 190, as illustrated in FIG. 1B.

As illustrated by way of example in FIGS. 1A and 1B, device 100 may further comprise a clasp actuator 180 and/or a pull wire 170. The pull wire 170 may be coupled to the clasp retainer ring 165 which is located within the clasp 150 and within the distal end 160 of the delivery device 190 such that upon actuation of the clasp by the clasp actuator 180, the clasp retainer ring 165 may retract from the clasp 150. Accordingly, upon actuation by the clasp actuator 180, the clasp 150 may transition into the closed configuration, in which the clasp 150 closes between the protruding elements 140 at the second end 130 of the band 110. As such, the clasp 150 and the band 110 may disconnect from the delivery device 190, thereby forming a loop.

According to another embodiment of the present disclosure, the band 110 may be configured to be passed through the spaces among the trabeculae between the papillary muscles and the wall of the ventricle. FIG. 3, for example, illustrates a device 300 comprising a band 310 having a clasp 320. The band 310 may be configured to be passed through the spaces among the trabeculae 330 between the papillary muscles 340 and the wall of the ventricle 350. In some embodiments of the present disclosure, two locations along the band may be attached together after the band has been passed around one, two, or more, papillary muscles in order to form a loop. In some embodiments, the attachment is configured such that the band or loop pulls the papillary muscles towards each other.

In some embodiments of the present disclosure, the band may be configured such that it does not contact the opposing faces of the papillary muscles. For example, the band may only contact the sides of the non-opposing surfaces of the papillary muscles. FIG. 3, for example, illustrates band 310 contacting only the sides of the non-opposing surfaces of the papillary muscles 340. Alternatively, the band may be configured to contact the non-opposing sides of the papillary muscles and to pull the papillary muscles towards each other.

In another embodiment of the present disclosure, the band may be configured to contact the papillary muscles such that opposing faces of the papillary muscles have no band material interposed between them. In FIG. 3, for example, the band 310 loops around the papillary muscles 340 such that there is no band material interposed between the papillary muscles 340. Accordingly, the band 310 may be configured such that when positioned around the papillary muscles 340, there is no portion of the band 310 intervening between the papillary muscles 340 around which the band 310 is positioned. In some embodiments, the band 310 may be configured such that when it pulls the papillary muscles 340 together, the papillary muscles 340 can contact each other with no portion of the band 310 or other foreign material between them.

In some embodiments of the present disclosure, the two locations of the attachment which forms the band into a loop may be at the first end and the second end of the band. The term "attachment" may refer to a clasp or any material used to hold the ends of the band together to form a loop. Referring back to FIG. 1A, for example, the two locations of the attachment which forms the band 110 may be at the first end 120 and the second end 130 of the band 110. In some embodiments of the present disclosure, the two locations of the attachment which forms the band 110 into a loop may be proximate the first end 120 and the second end 130 of the band 110. Alternatively, the attachment which forms the band 110 into a loop may be closer to the first end 120 than to the second end 130. In other embodiments, the attachment which forms the band 110 into a loop may be in a fixed position relative to the first end 120 of the band 110, and its position relative to the second end 130 of the band 110 can be varied in order to adjust the size of the band 110.

Figure 2:
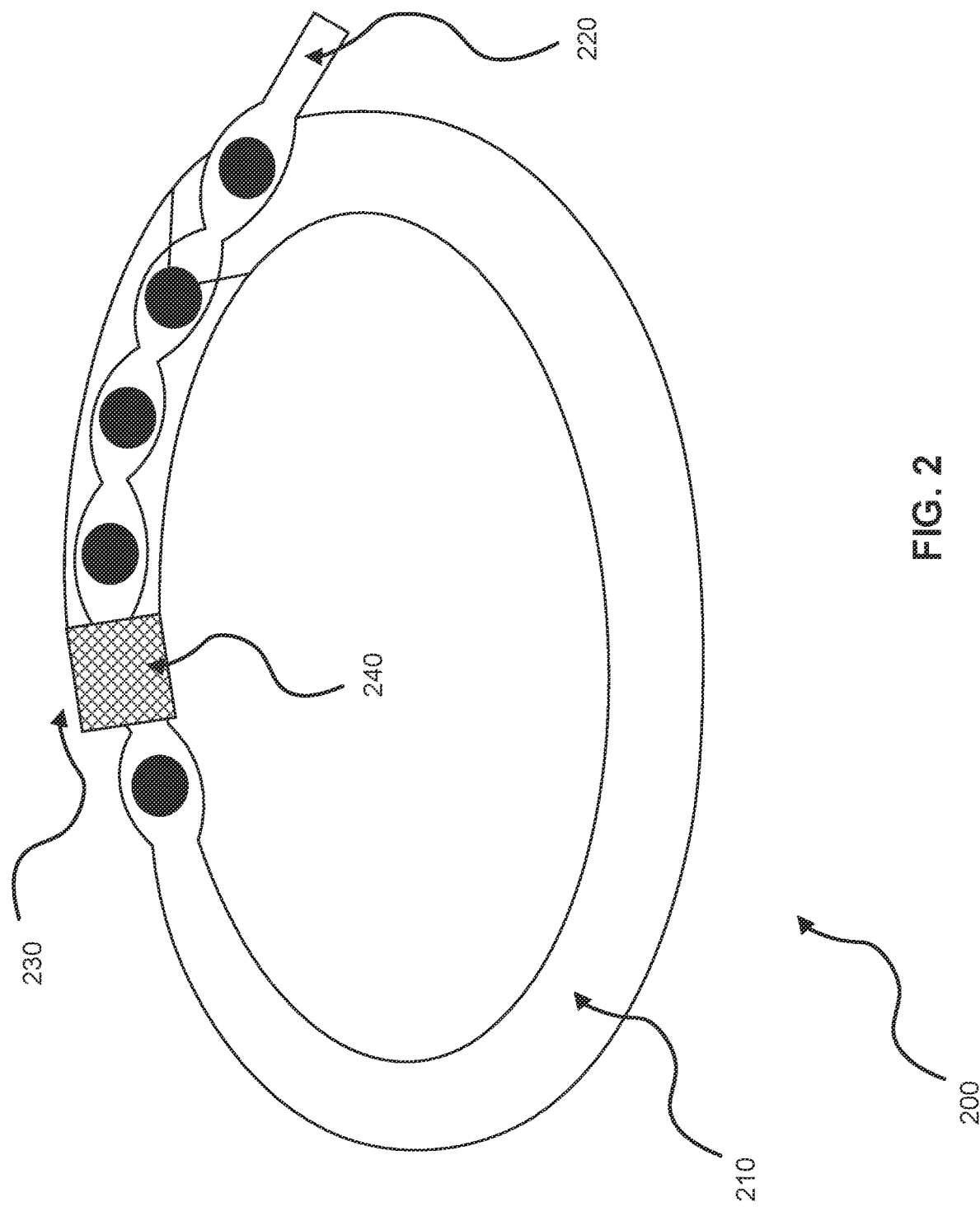
FIG. 2 illustrates an exemplary band for repositioning papillary muscles in a loop, in accordance with another embodiment of the present disclosure.

FIG. 2, for example, illustrates a device 200 comprising a band 210. The band 210 comprises a first end 230, a second end 220, and a clasp 240. The clasp 240 may be located in a fixed position relative to the first end 230 of the band 210. The position of the clasp 240 relative to the second end 220 of the band 210 can be varied in order to adjust the size of the loop formed by the band 210. Optionally, the attachment which forms the band may attach one end of the band to any location along the band. In yet another embodiment, the attachment which forms the band may attach any two locations along the band together.

In accordance with the embodiments of the present disclosure, the band may further comprise a clasp. FIGS. 1A-1C, for example, illustrate a band 110 comprising a clasp 150 that forms the attachment between the first end 120 and the second end 130 along the band 110 in order to form a loop. In some embodiments, the clasp 150 may be provided with the band 110 and attached to the band 110. In other embodiments, the clasp 150 may be attached to or near the first end 120 of the band 110. In other embodiments, the clasp 150 may not be attached to the band 110 until the clasp 150 is actuated. When the clasp 150 is actuated, the clasp 150 may attach to the first end 120 and the second end 130 of the band 110 to form a loop (an example of which is shown in FIG. 2). In some embodiments of the present disclosure, device 100 may further comprise a clasp actuator (not shown) that may be used to actuate the clasp 150. The position of the clasp 150 relative to the second end 130 of the band may be varied in order to adjust the size of the loop formed by the band 110 until the clasp actuator (not shown) actuates the clasp 150. For example, once actuated, the clasp 150 may transition from an open configuration (an example of which is shown in FIG. 1A) to a closed configuration (an example of which is shown in FIGS. 1B and 1C). Alternatively, the length of the loop formed by the band 110 may be adjusted over a range of at least 5 mm, at least 8 mm, or at least 10 mm.

In some embodiments, the clasp may be attached to a wall of the band near one of the ends of the band. FIG. 2, for example, illustrates clasp 240 attached to a wall of the band 210 near the first end 230. The clasp 240 may be attached to band 210 at the first end 230, for example, before implantation into the heart. The second end of the band may pass through or past the clasp 240. For example, referring to FIG. 2, the second end 220 of the band 210 may pass through or past the clasp 240. Upon actuation of the clasp 240 after implantation into the heart, the actuation may cause the clasp 240 to grasp a portion of the band 210 that has passed through or past the clasp 240, thereby locking the second end 220 of the band 210 in a fixed position relative to the first end 230 of the band 210. Accordingly, a loop may be formed.

The width or diameter of the band may be between about 2 mm and about 5 mm. For example, the width or diameter of the band may be between about 3 mm and about 4 mm. The width of the band may be constant along the length of the band. Alternatively, the width of the band may vary along its length and may be larger at one end than at the other end. For example, the end of the band to which the clasp is connected may have a larger width than the end of the band that is inserted into the clasp. Accordingly, the end of the band inserted into the clasp may have a smaller width.

In some embodiments, the band may comprise a tube. In some embodiments, the clasp may be located inside a first end of the band and/or may be attached to the wall of the band near the first end. FIG. 2, for example, illustrates the clasp 240 attached to a wall of the band 210 near the first end 230. The second end of the band may pass through or past the clasp within the inner lumen of the band. For example, the second end 220 of the band 210 may pass through or past the clasp 240 within the inner lumen of the band 110. Upon actuation of the clasp 240 after implantation into the heart, the actuation may cause the clasp 240 to grasp a portion of the band 210 that has passed through or past the clasp 240, thereby locking the second end 220 of the band 210 in a fixed position relative to the first end 230 of the band 210. Accordingly, a loop may be formed. In some embodiments, the clasp may be positioned within the band such that the band prevents the clasp from contacting the heart tissue. FIG. 3, for example, illustrates device 300 comprising a band 310 and a clasp 320 located within the band 310. The band 310 may prevent the clasp 320 from contacting the surrounding tissue in the ventricle 350 of the heart.

According to the exemplary embodiments of the present disclosure, the clasp may be configured to fix a length of the loop to correspond to the unique anatomy of the patient. In addition, the clasp may be configured to be actuated within the heart of the patient. Accordingly, the clasp may be configured to be selectively actuatable to fix a length of the loop formed by the band such that the loop corresponds to the unique anatomy of the patient. As discussed above, the clasp may have multiple mechanical configurations. For example, during insertion and positioning of the band within the heart of the patient, the clasp may be in an open configuration (an example of which is shown in FIG. 1A). In the open configuration, for example, an insertion cable (not shown) and a second end of the band may move freely through or past the clasp. Once the band is properly positioned and adjusted, a clasp actuator may be used to actuate the clasp, reconfiguring it to a closed configuration (an example of which is shown in FIGS. 1B and 1C). In the closed configuration, for example, the clasp may grasp a portion of the band that has passed through or past the clasp, thereby preventing the band from moving relative to the clasp and forming a loop.

Figure 4:
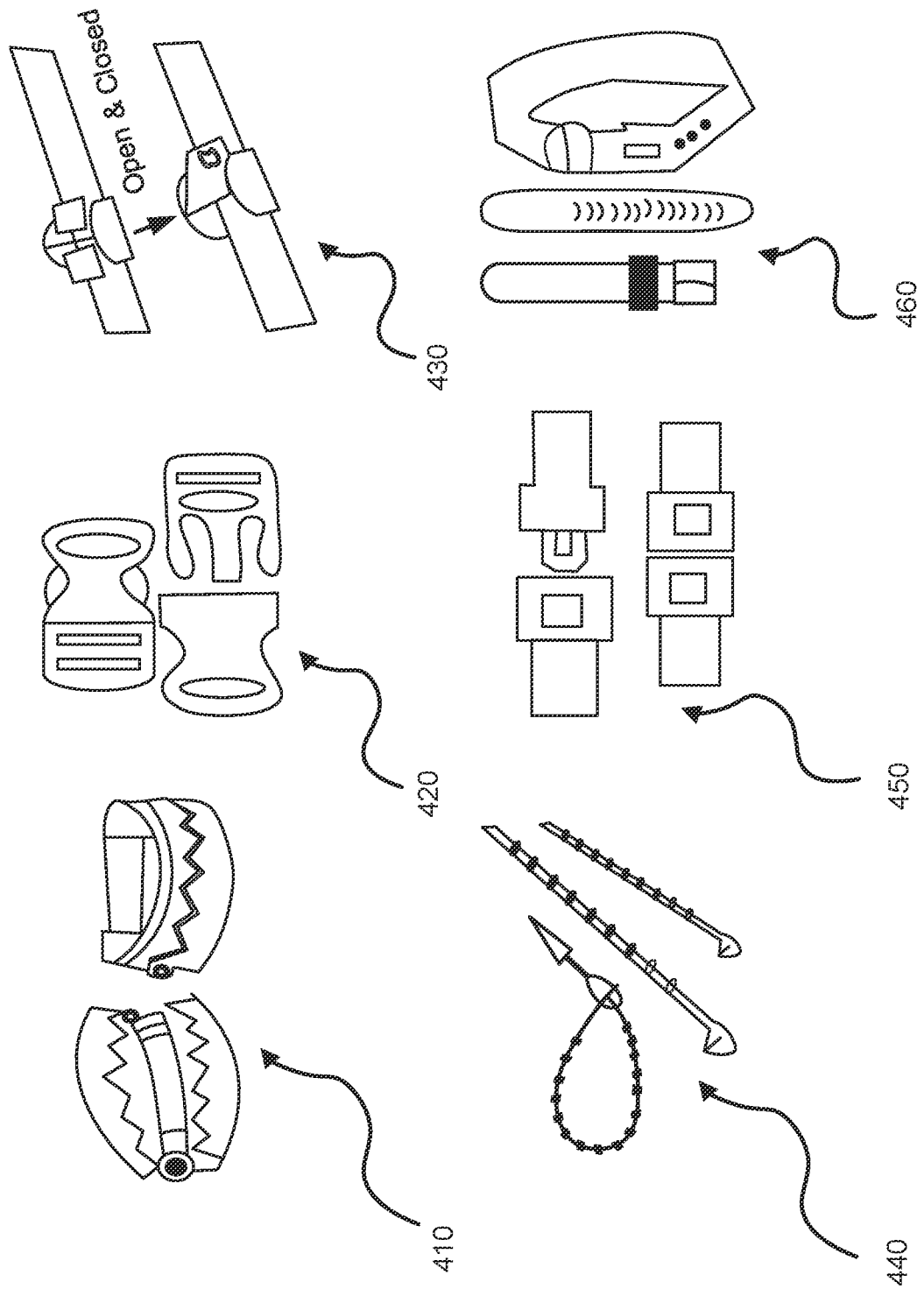
FIG. 4 illustrates an exemplary embodiment of an adjustable clasp, in accordance with an embodiment of the present disclosure.

The clasp may be a clip, grasper, catch, fastener, buckle, or any other type of clasp that is capable of attaching one location of the band to another location of the band. FIG. 4 illustrates various exemplary embodiments of the clasp in open and closed configurations. For example, as seen in FIG. 4, the clasp may be a bear trap type clasp 410, a clip type clasp 420, a fastener type clasp 430, a self-locking zip tie type clasp 440, a buckle type clasp 450, a fastener type clasp 460, or any other type of clasp capable of attaching one location of the band to another location of the band.

In some embodiments, the clasp may be made of a metal, for example, spring steel, stainless steel, and/or nitinol. In other embodiments, the clasp may be made of a polymer material, or any other material with the mechanical properties necessary to provide an open configuration and a closed configuration. In some embodiments, the clasp may be biased towards a closed configuration and may be elastically deformed into an open configuration until being actuated by the clasp actuator. For example, the clasp actuator may allow the clasp to return to the closed configuration. A second end of the band may be passed through or past the clasp in the open configuration. Accordingly, when the second end of the band is properly positioned, the clasp actuator may allow the clasp to elastically return to the closed configuration such that the clasp may grasp the band and lock the band in place, thereby forming a loop.

In other embodiments, the clasp may be biased toward an open configuration and may be deformed into a closed configuration when actuated by the clasp actuator. For example, the clasp actuator may force the clasp into the closed configuration. In such embodiments, the second end of the band may pass through or past the clasp in the open configuration. When the second end of the band is properly positioned, the clasp actuator may force the clasp into the closed configuration such that the clasp may grasp the band and lock the band in place, thereby forming a loop.

Figure 5:
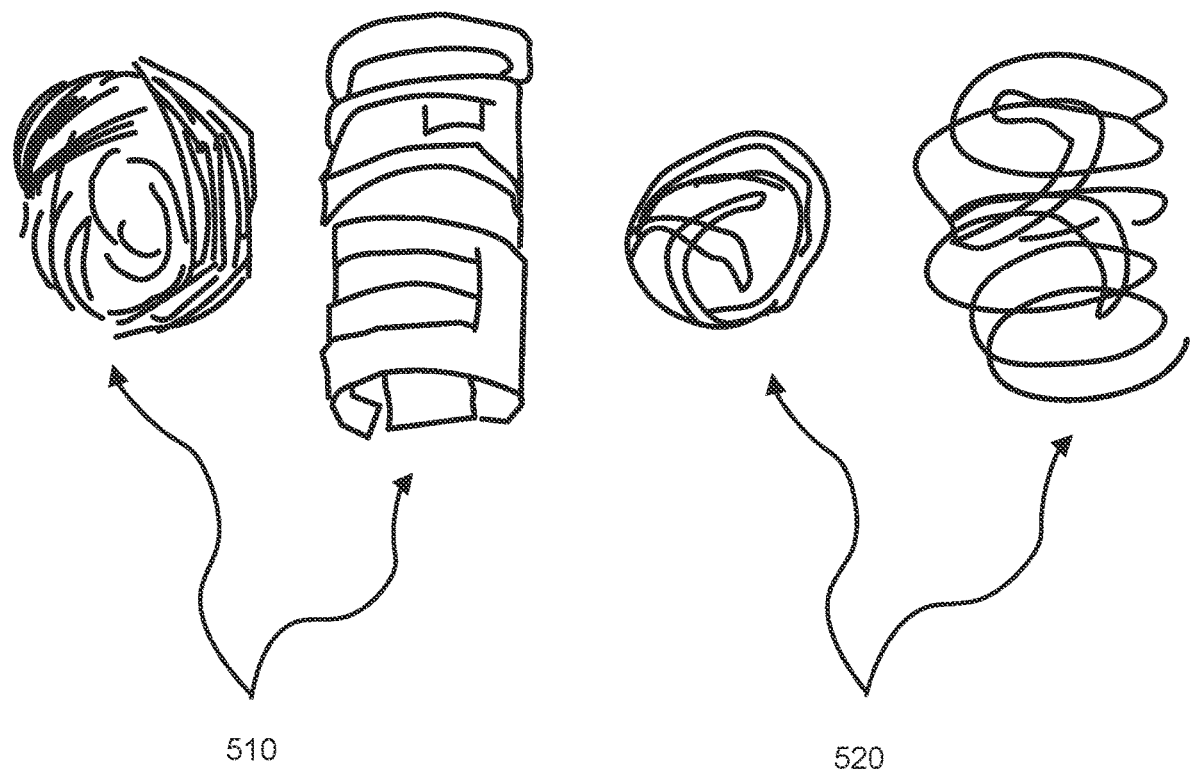
FIG. 5 illustrates another exemplary embodiment of an adjustable clasp, in accordance with an embodiment of the present disclosure.

According to another embodiment of the present disclosure, the clasp may be a cylinder with elastic elements that extend inward into the inside of the cylinder. In the open configuration, the elastic elements of the clasp may be held outwards in or near the wall of the cylinder. FIG. 5, for example, illustrates various embodiments of the clasp that may be a cylinder. For example, a clasp 510 may be manufactured from a cut tube in which the elastic elements are cut from the wall of the tube and then bent inwards. The clasp 510 may be configured to grasp a portion of the band at any location along the band or the clasp 510 may be configured to grasp a graspable component or feature located at a certain location along the band. The clasp 510 may be held in the open configuration by a tube (not shown) placed within the clasp 510. The clasp 510 may be actuated to return to its closed configuration by removing the tube from within the clasp 510.

Alternatively, a clasp 520 may be made from bent wire, such as a coil spring, and the elastic elements may be portions of the bent wire that are configured to extend inwards into the inside of the cylinder. The clasps 510 and 520 may be flexible so that the band in the region of the clasps 510 and 520 remains flexible. This flexibility may be achieved by the design of the bent wire spring or by cuts in the wall of the cut tube configured to add flexibility to the tube.

Figure 6:
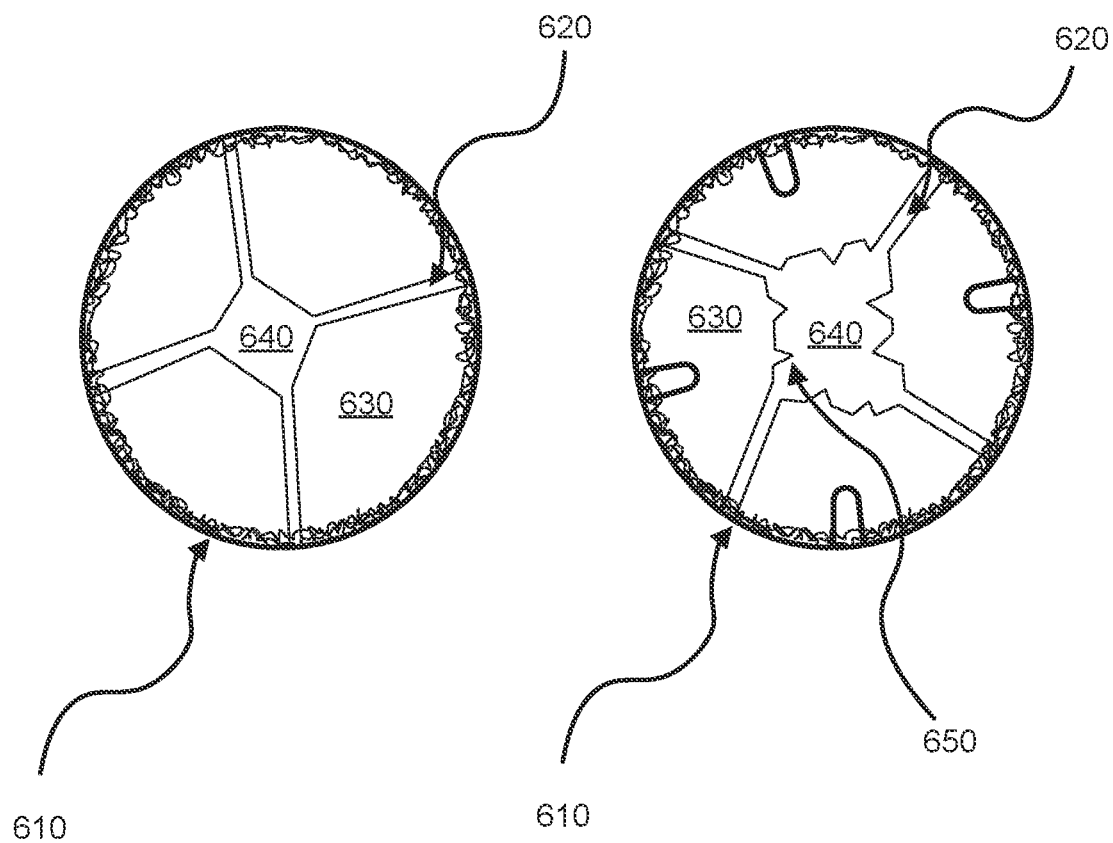
FIG. 6 illustrates another exemplary embodiment of an adjustable clasp, in accordance with an embodiment of the present disclosure.

In another embodiment, the clasp may be a disc with a plurality of cuts that form a plurality of leaves. The plurality of leaves may rotate out of the plane of the disc. FIG. 6, for example, illustrates clasp 610 with a plurality of cuts 620 that form a plurality of leaves 630. The perimeter of the clasp 610 may remain intact and the leaves 620 may be connected to the clasp 610 near the perimeter such that when the leaves 620 rotate out of the plane of the clasp 610, the leaves 620 may leave an open channel 640 through the middle of the clasp 610. The leaves 620 may be configured such that when an object (not shown) is passed in one direction through the open channel 640 through the middle of the clasp 610, the leaves 620 may press against the object and prevent or reduce the likelihood of the object passing back in the opposing direction through the open channel 610. In another embodiment, the leaves 620 may comprise at least one spike 650 at the region that contacts the object (not shown) that is passing through the open channel 640. Accordingly, if the object passing through is capable of being penetrated, spike 650 may penetrate the object and increase the ability of the clasp 610 to grasp the object passing through the clasp 610.

While only one clasp 610 is illustrated in FIG. 6, multiple clasps 610 may be used together in order to increase the strength with which the clasps 610 may grasp an object passing through them. Alternatively, a single clasp 610 may comprise multiple layers of leaves 630, thereby increasing the strength with which the clasp 610 may grasp an object passing through it. Such a multi-layered clasp may be made flexible such that a portion of a band, to which the clasp is connected, may remain flexible. Clasp 610 may be manufactured by cutting or stamping the form of the clasp 610 out of a flat sheet or by cutting the form of the clasp 610 out of a tube and bending the leaves 630 inward.

In some embodiments, the clasp may be made of a plurality of panels. FIGS. 7A-7B, for example, illustrate clasp 710 comprising a plurality of panels 720. The panels 720 may comprise a plurality of spikes 730 protruding from the panels 720. The spikes 730 may press against each other to grasp a band, for example, passing between the panels 720. The panels 720 may be connected at their edges by elastic components that induce the panels 720 to press against each other. The panels 720 may be flexible such that they naturally press flat against each other, but can be elastically deformed into a curved shape, as illustrated by way of example in FIGS. 7A-7B.

The clasp 710 may be cut from a tube with the panels 720, and the elastic components that hold the panels 720 together at their edges may also be cut from the same tube. The spikes 730 protruding from the panels 720 may be cut from the wall of the panels 720 and bent inwards to form the protruding spikes 730. The spikes 730 and/or the panels 720 may be elastically deformed outward into an open configuration of the clasp 710 by placing an inner tube (not shown) between the panels 720. Upon removal of the inner tube, the spikes 730 and the panels 720 may return to a closed configuration, in which the spikes 730 may protrude perpendicularly to the panels 720, and the panels 720 may press against each other.

In other embodiments, the clasp may be composed of a ring with spikes protruding from the ring. FIG. 7C-7D, for example, illustrate clasp 740 comprising a ring 750 with a plurality of spikes 760 protruding from the ring 750. In a closed configuration (examples of which are shown in FIG. 7C-7D), the spikes 760 may lay across part (FIG. 7C) or all (FIG. 7D) of the inside of the ring 750. In an open configuration, the spikes 760 may be rotated out of the plane of the ring 750 and may allow an object, such as a band, to pass through the center of the ring 750. The spikes 760 may be biased towards the closed configuration and may be elastically rotated into the open configuration during positioning and adjustment of a band around the papillary muscles. Then, the spikes 760 may be allowed to return to the closed configuration upon actuation by a clasp actuator. Alternatively, the spikes 760 may be biased toward the open configuration and may be forcibly bent into the closed configuration upon actuation by the clasp actuator. In some embodiments, the spikes 760 may be configured to rest against the ring 750 or protrusions (not shown) extending from the ring 750 in the closed configuration such that the spikes 760 may not rotate past the plane of the ring 750.

As discussed above, the clasp may be locked into a closed configuration upon actuation by a clasp actuator. In some embodiments of the present disclosure, the clasp actuator may be configured to enable actuation of the clasp remotely, such as from outside of the heart. In other embodiments, the clasp actuator may be configured to enable actuation of the clasp from outside of the body of the patient. Accordingly, the clasp actuator may be configured to enable the user to actuate the clasp from a location distant from the clasp.

Figure 8:
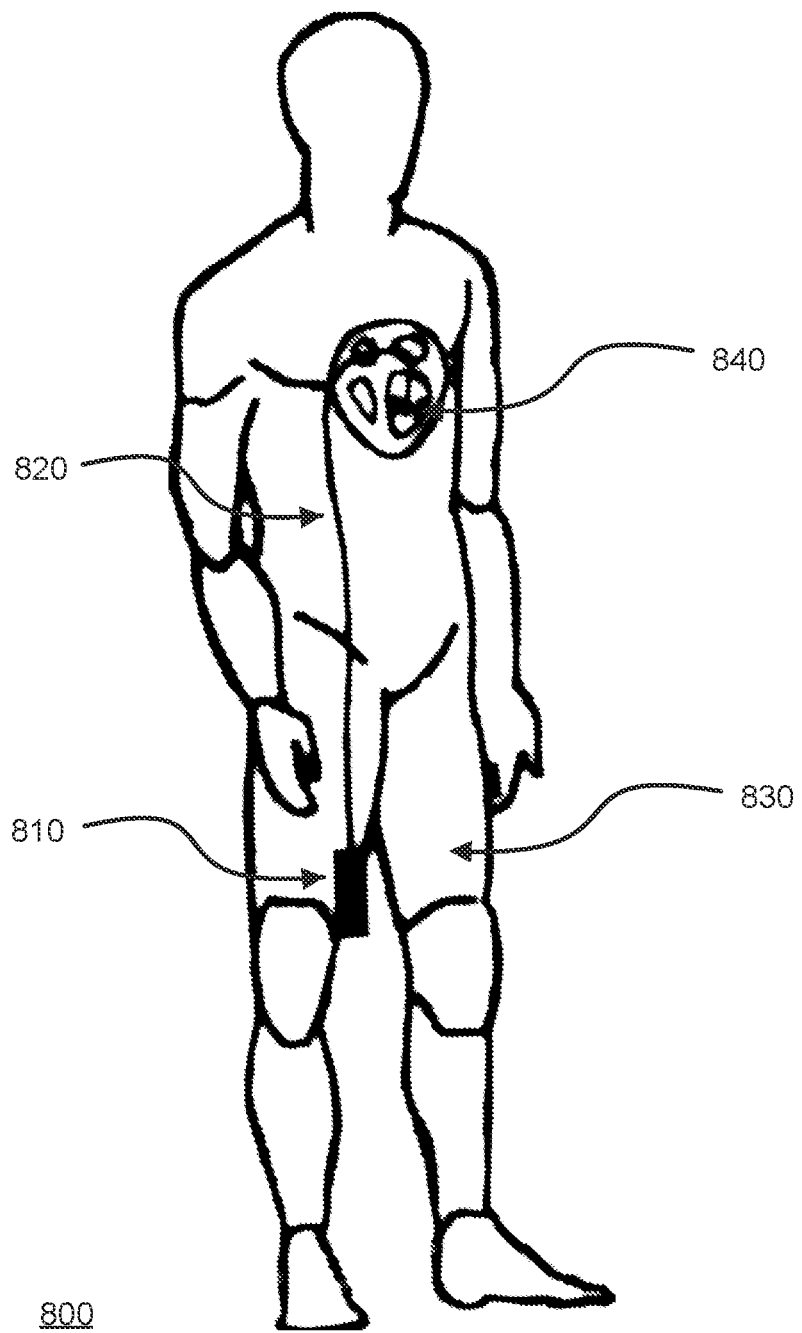
FIG. 8 illustrates an exemplary body of a human in which embodiments of the present disclosure may be employed.

FIG. 8, for example, illustrates a clasp actuator 800 that may enable the user to actuate the clasp 840 from outside of the body 830. The clasp actuator 800 may include pull wires, rotating shafts, rotating tubes, moveable shafts, moveable tubes, electrical actuators, pneumatic actuators, hydraulic actuators, or any other means of providing actuation remotely in order to actuate a clasp located within the heart from outside of the body. For example, clasp actuator 800 may be configured to allow the actuation of clasp 840 via a flexible catheter 820 from outside of the body 830. In some embodiments, the clasp actuator 800 may further include a trigger 810 located outside of the body 830 that can be used to actuate the clasp 840 located inside the heart.

In some embodiments of the present disclosure, the first end of the band may be mounted on a delivery device in order to encircle the band around the papillary muscles. The delivery device may incorporate part of or all of the clasp actuator within the device. Further, the delivery device may include a rigid or flexible tube. Alternatively, the delivery device may comprise a tube having rigid portion(s) and flexible portion(s). The delivery device may include a tube or a conduit that passes through a side wall of the band configured to form a loop around the papillary muscles.

Figure 9:
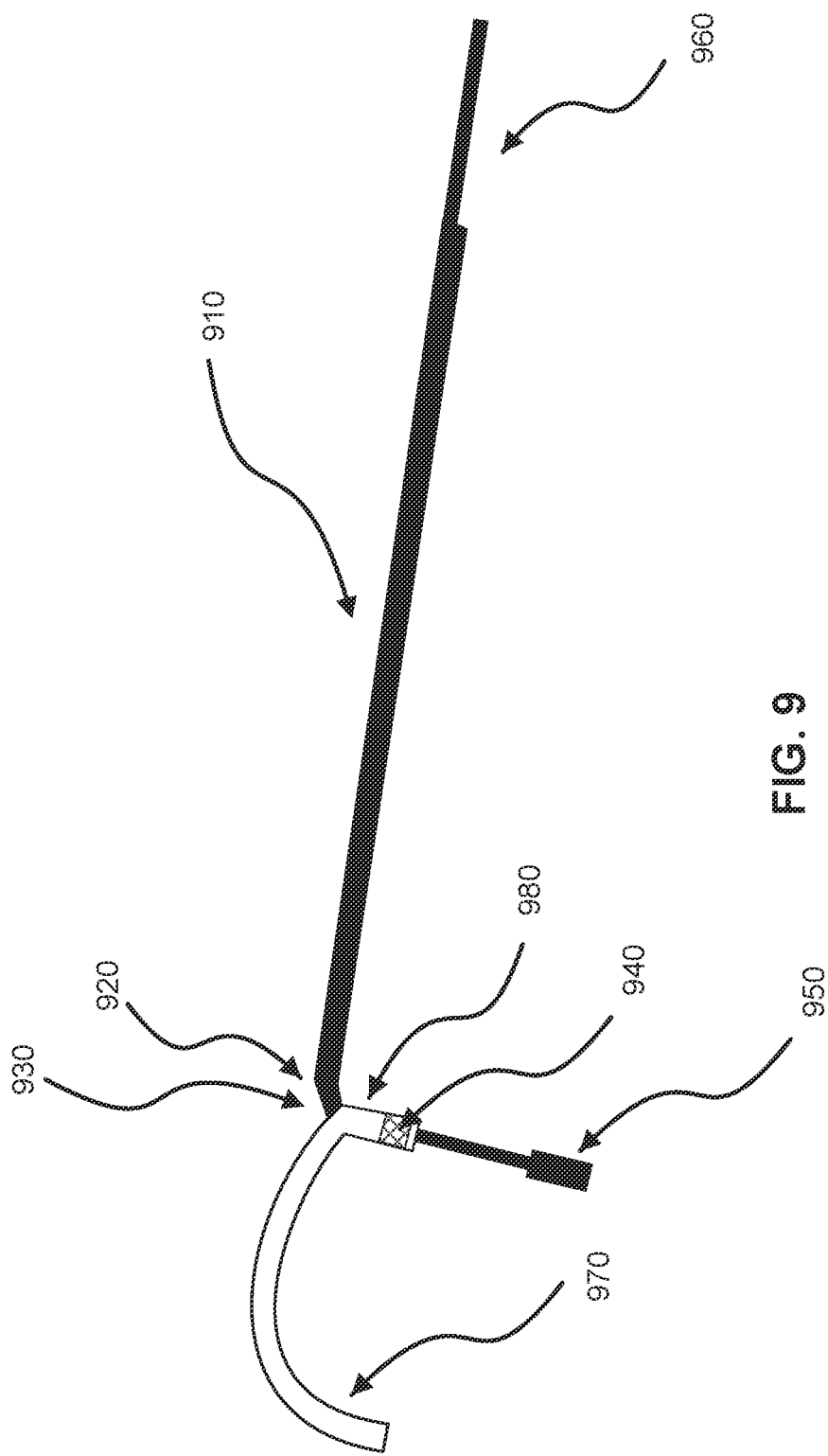
FIG. 9 illustrates an exemplary delivery device in which embodiments of the present disclosure may be employed.

By way of example, FIG. 9 illustrates an exemplary delivery device 910 connected near the first end 980 of the band 970. The band 970 may comprise an opening 930 on a side wall of the band 970, through which the removable delivery device 910 may pass. The delivery device 910 may pass through the wall of the band 970 near the first end 980 such that a portion of the delivery device 910 is within a portion of the band 970 near the first end 980. The portion of the band 970 that comprises the delivery device 910 within the band 970, e.g., distance from the first end 980 of the band 970 to the location where the delivery device 910 passes through the opening 930 of the band 970, may be in the range of about 5 mm to about 25 mm. For example, the distance may be in the range from about 10 mm to about 15 mm. In some embodiments, clasp 940 may be located within 25 mm, 15 mm, 10 mm, or 5 mm from the first end 980 of the band 970. The clasp 940 may be located within the portion of the band 970 that has the delivery device 910 within it. In some embodiments, the components of the clasp actuation mechanism, for example pull wires or a clasp retainer ring, that engage the clasp may be located in the portion of the delivery device 910 that is within the band 970. The clasp 940 may be located at one end of the delivery device 910. The other end of the delivery device 910 may be located outside of the patient's body. In other embodiments, the clasp actuation mechanism may include an elongated member that may pass through the delivery device 910.

The delivery device 910 may further include a region proximal to the location where the delivery device 910 passes through an opening 930 of the band 970 that may be flexible and/or actively deflectable. The deflection of the deflectable region 920 may be controllable between at least 0 degrees and 90 degrees. In some embodiments, the delivery device 910 may further include an insertion cable threader 960 protruding from both ends of the delivery device 910. One end of the threader 960 protruding from one end of the delivery device 910 may comprise a grasper 950 configured to grasp an insertion cable (not shown) coupled to the band 970. In some embodiments, the grasper 950 may removably grasp the insertion cable coupled to the band 970. The other end of the threader 960, which protrudes from the other end of the delivery device 910, may be configured to be pulled to pull the insertion cable (not shown) through the delivery device 910. The insertion cable may be released from the threader 960 after having been pulled through the delivery device 910.

Figure 10:
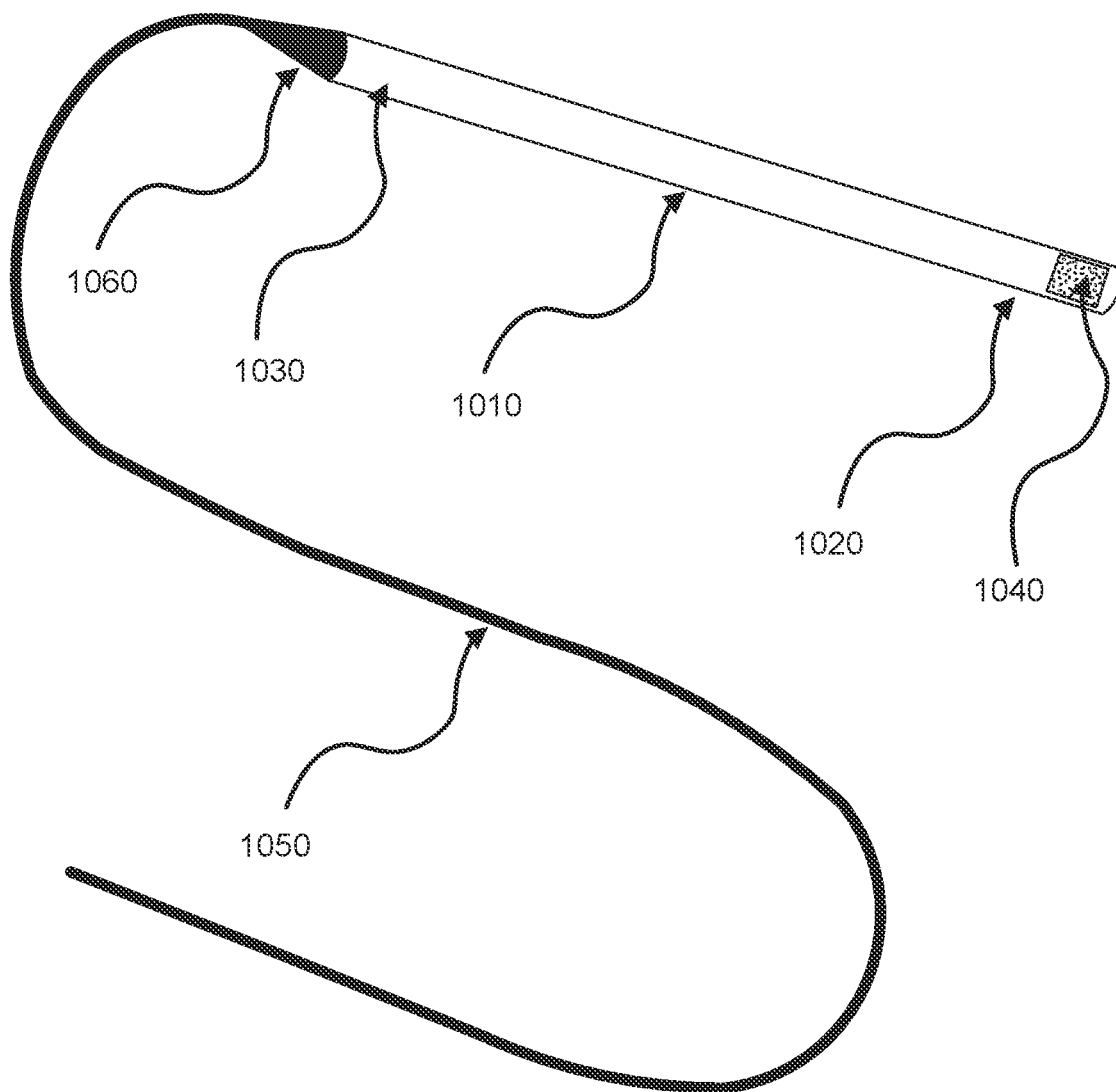
FIG. 10 illustrates an exemplary delivery device with an exemplary insertion cable, in accordance with the embodiments of the present disclosure.

In some embodiments, an insertion cable coupled to a band may be provided in order to aid in the insertion of the band into the heart. By way of example, FIG. 10 illustrates a device 1000 comprising an insertion cable 1050 coupled to a band 1010. The insertion cable 1050 may aid in the insertion of the band 1010 into the heart and around the papillary muscles. In some embodiments, the insertion cable 1050 may aid in the insertion of the band 1010 into a clasp 1040.

In accordance with the embodiments of the present disclosure, a distal end of the insertion cable 1050 may be removably connected to the second end 1030 of the band 1010. The insertion cable 1050 may be configured to adjust the size of a loop formed by the band 1010 encircling the papillary muscles. The insertion cable 1050 may be flexible, such that the insertion cable 1050 may aid in guiding the band 1010 around the papillary muscles to form a loop. The proximal end of the insertion cable 1050 may be configured to be passed through the spaces among the trabeculae between the papillary muscles and the wall of the ventricle. Further, the insertion cable 1050 may fit into the first end 1020 of the band 1010 and through or past the clasp 1040 when the clasp 1040 is in an open configuration. Alternatively, the insertion cable 1050 may fit into a distal end of a delivery device (an example of which is illustrated in FIG. 9) which may be located within the first end 1020 of the band 1010.

In an alternative embodiment, the insertion cable 1050 may further comprise an insertion cable release trigger (not shown) located at or near the proximal end of the insertion cable 1050. The distal end of the insertion cable 1050 may be configured to separate from the second end 1030 of the band 1010 upon actuation of the insertion cable release trigger. In some embodiments, the insertion cable release trigger may be the proximal end of a wire or tube (not shown) extending through the lumen of the insertion cable 1050 which is pulled, pushed, rotated, or otherwise manipulated, to actuate the release of the insertion cable 1050.

The band 1010 may be releasably connected to the insertion cable 1050. For example, the insertion cable may be releasably connected to the band 1010 by way of an insertion cable adapter 1060. The insertion cable adapter 1060 may be attached to the second end 1030 of the band 1010. In other embodiments, the insertion cable adapter 1060 may be permanently attached to the second end 1030 of the band 1010, and the insertion cable 1050 may be removably attached to the insertion cable adapter 1060.

Figure 11:
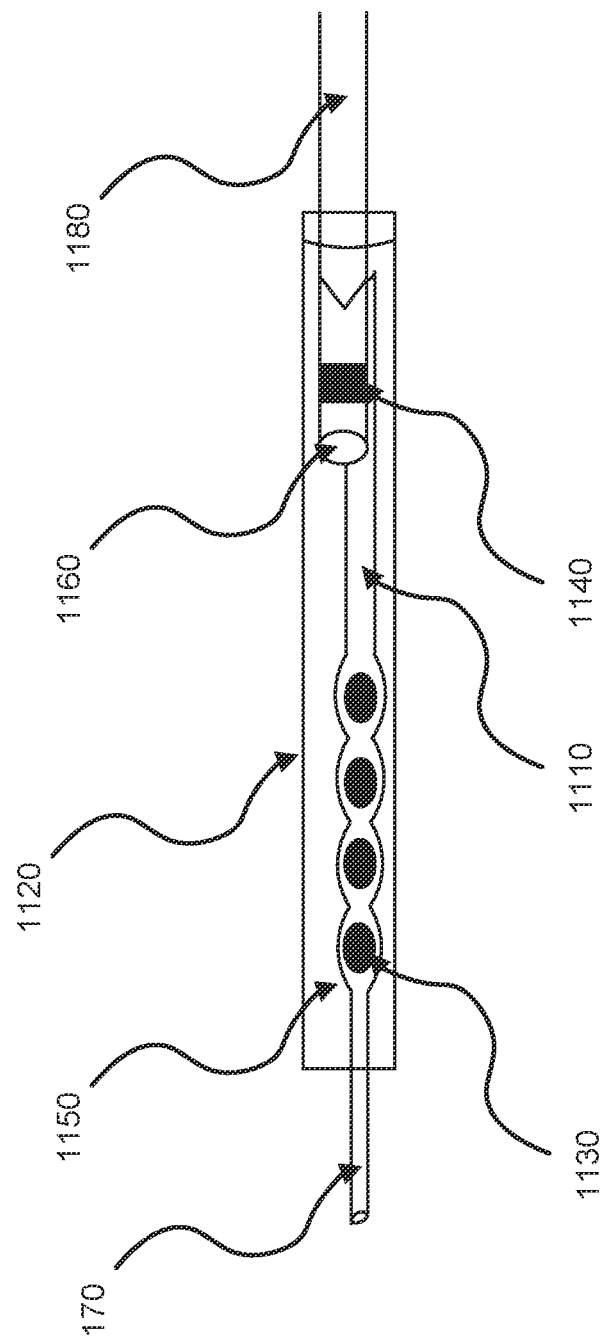
FIG. 11 illustrates another exemplary delivery device in which embodiments of the present disclosure may be employed.

In some embodiments, at least a portion of the band may be pre-loaded into a tube. By way of example, FIG. 11 illustrates at least a portion of a band 1110 pre-loaded into a tube 1120. Alternatively, at least a portion of the band 1110, at least a portion of the insertion cable 1170 attached thereto, and at least a portion of an attached delivery device 1180 may be pre-loaded into a tube 1120.

Referring back to FIG. 10, the band 1010, a delivery device (not shown), and the insertion cable 1050 may be configured for insertion into the heart via a transthoracic approach, a transarterial approach, a transveous approach, a transarterial/transaortic approach, a transveous/transseptal/transmittal approach, or any other surgical or minimally invasive approach to the heart.

In some embodiments, a clasp 1040 may be attached at or near the first end 1020 of the band 1010 and may be configured to grasp the band 1010 at a location where the band 1010 passes through or past the clasp 1040. Accordingly, the amount of band adjustment necessary to form a loop of a desired circumference may be independent of the length of the clasp 1040.

As discussed above, the clasp 1040 may be attached at or proximate the first end 1020 of the band 1010 and may be configured to grasp a graspable component or feature located at or proximate the second end 1030 of the band 1010, or at any location along the band 1010. In other embodiments, multiple graspable components or features may be located at multiple locations along the band 1010. The clasp 1040 may be configured to grasp a graspable component or feature at multiple locations or at any location along the length of the clasp 1040. In some embodiments, the amount of band adjustment necessary to form a loop of a desired circumference may be dependent upon the length of the clasp 1040 and the number of locations of the graspable components or features since a graspable component or feature may need to be within the clasp to be grasped (an example of which is shown in FIGS. 1A-1C).

In some embodiments, the clasp 1040 may interact with the material of the band 1010 itself in achieving the grasping. In other embodiments, there may be a component or feature at a location in or on the band 1010 that the clasp 1040 may grasp. The graspable component or feature that the clasp 1040 may grasp may be movable relative to the position of the second end 1030 of the band 1010.

Clasp 1040 may be attached to the wall of the band 1010 at or proximate the first end 1020 of the band 1010 using glue or adhesive. Additionally or alternatively, clasp 1040 may be attached using melting or thermal bonding to the wall of the band 1010, using suturing, stitching, or sewing to the wall of the band 1010, using clasp elements that couple the clasp 1040 onto the wall of the band 1010, or any other attachment method or combination of attachment methods that can attach the clasp 1040 to the wall of the band 1010.

By way of example, FIG. 11 illustrates a band 1110 comprising a plurality of graspable components 1130 at or proximate the second end 1150 of the band 1110. The graspable elements 1130 may be objects, soft or hard balls made of plastic, metal, and/or polymer, protrusions, spikes, or any material that is capable of being grasped by a clasp. At or proximate the first end 1160 of the band 1110, a clasp 1140 may be provided that is configured to grasp at least one of the graspable components 1130. The second end 1150 of the band 1110 may be pulled through the first end 1160 of the band 1110. Then, the clasp 1140 may be configured to transition from an open configuration to a closed configuration upon actuation by a clasp actuator to grasp at least one of the graspable components 1130 in order to form a loop of a desired circumference, preferably based on the unique anatomy of the patient.

Referring back to FIG. 1A-1B, in some embodiments, the distal end of the delivery device 190 may include a clasp retainer ring 165 within an outer tube of the delivery device 190. The distal end of the outer tube may be located proximally to the clasp 150 and have a diameter such that the clasp 150 cannot fit into the outer tube. The clasp retainer ring 165 may extend distally beyond the distal end of the outer tube and be positioned within the clasp 150, holding the clasp 150 in an open configuration (an example of which is illustrated in FIG. 1A). Accordingly, the clasp 150 may be biased towards a closed configuration and may be held in the open configuration by the clasp retainer ring 165 located within the clasp 160. The actuation of the clasp 150 may include pulling the clasp retainer ring 165 proximally relative to the outer tube such that the clasp retainer ring 165 is retracted from within the clasp 150 into the outer tube, thereby allowing the clasp 150 to return to a closed configuration (an example of which is illustrated in FIG. 1B). Additionally or alternatively, pull wires or a pull-tube may be connected to the clasp retainer ring 165, and may run through the delivery device 190 to the proximal end of the delivery device 190. At the proximal end of the delivery device 190, the pull wires or pull-tube may be connected to a trigger that may pull the pull wires proximally relative to the delivery device 190 in order to retract the clasp retainer ring 165 into the outer tube. After actuation of the clasp 150, the delivery device 190 may be removed from the band 110.

In some aspects, the insertion cable (an example of which is shown in FIG. 10) may comprise a tube with a wire located within the tube. The distal end of the tube may have longitudinal slits splitting the wall of the tube into multiple flaps. The flaps may have thickened walls at their distal tips such that when the wire is inside the tube, the distal end of the tube may be unable to fit through a hole whose diameter is the same as the outer diameter of the tube. However, when the wire is removed from the distal end of the tube, the distal end of the tube may be able to fit through a hole whose diameter is the same as the outer diameter of the tube. In other embodiments, the distal region of the wire that holds the flaps outward may have a larger diameter than the rest of the wire. In some aspects, the tube may be a coil with a solid tubular region at the distal end. The coil may be tightly wound to avoid compression and have a wire or ribbon running through the coil connected at both ends to avoid stretching.

According to one embodiment of the present disclosure, the flaps may be formed by cutting through the wall of the tube near the distal end. The thickening of the walls of the distal tips of the flaps may be formed by bending the distal tips of the flaps back on themselves one or more times. The distal portion of the tube of the insertion cable from which the flaps are formed may be made of metal, polymer, or plastic or any other material capable of being formed into flaps with thickened walls.

In other aspects, the flaps may have a radially outward step before the thickened portion. Accordingly, the insertion cable may not be allowed to pass through a hole whose diameter is the same as the outer diameter of the tube without applying excessive force on the wire that is holding the flaps outwards. Additionally or alternatively, the flaps may be biased radially inwards so that when the wire is not located within the region of the tube containing the flaps, the flaps may bend inwards, and the tube may pass freely through a hole whose diameter is the same as the outer diameter of the tube.

Referring back to FIG. 10, an insertion cable adapter 1060 may be attached to the second end 1030 of the band 1010. The insertion cable adapter, for example, may have a channel (not shown) through it with a diameter equal to or slightly greater than the outer diameter of the tube of the insertion cable 1050. A region of the channel may have a diameter large enough to fit the distal end of the tube with the wire inside of it. Diameters of the tube, the thickened flaps at the distal end of the tube, and the narrow and wide regions of the channel in the adapter may be configured such that, when the outer tube is inside the channel in the adapter and the wire is inside the distal end of the tube, the tube may become locked in the adapter because its distal end cannot fit through the narrow region of the channel. As such, when the wire is removed from the distal end of the tube, then the tube may be removed from the adapter. The wire may extend through the tube, additionally or alternatively extending beyond the proximal end of the tube, so that the wire can be pulled from the proximal end to retract the wire out of the distal end of the tube in order to detach the insertion cable from the adapter. Additionally or alternatively, the proximal end of the wire may be attached to a puller, which may be removably attached to the proximal end of the tube. Accordingly, when the puller is removed and pulled away from the tube, the puller may pull the wire along with it, thereby retracting the wire from the distal end of the tube. In some aspects, the puller may be removably attached to the proximal end of the tube by being screwed onto or screwed into the distal end of the tube. Alternatively, the puller may not be at the distal end of the tube but may be located in the middle of the tube near the distal end.

In some aspects, the insertion cable may be removably connected to the insertion cable adapter by one or more wires, fibers, or other thin elongated elements passing out through the holes in the wall of the tube and passing back into the tube through holes in the insertion cable adapter and in the wall of the tube. The wires, fibers, or other thin elongated elements may extend through the tube and may be pulled at or near the proximal end of the tube to remove them from the holes, thereby releasing the connection of the insertion cable to the insertion cable adapter. The insertion cable may be a suture, string, fiber, or wire that is cut in order to detach the insertion cable from the second end of the band. The insertion cable may be a flexible torque cable or torque tube with a screw at its distal end. The screw at the distal end of the insertion cable may be screwed into the insertion cable adapter connected to the second end of the band. Accordingly, turning the proximal end of the insertion cable may cause the distal end of the insertion cable to unscrew from the insertion cable adapter and detach from the band. In other embodiments, the flexible torque cable or torque tube may be covered by a flexible braided tube to enhance its tensile strength. The flexible braided tube may be made of metal, polymer, silk, or any other biocompatible material that can be made into a fine braid and used to cover the torque cable or torque tube adding tensile strength.

According to another embodiment of the present disclosure, a cardiac implant is provided. The cardiac implant may comprise a papillary band formed of a tube with an opening in a side wall of the tube and a removable conduit passing through the opening. The cardiac implant may additionally comprise a clasp associated with the band. The clasp may be configured to be actuated by an elongated member, which passes through the removable conduit. Upon actuation, the clasp may attach two locations along the band to each other forming the band into a loop. The clasp may be located at a distal end of the conduit, and the proximal end of the conduit may be located outside of the patient's body. The removable conduit may be configured to be removed from the tube after actuation of the clasp.

As discussed above, the band may be configured to contact non-opposed surfaces of the papillary muscles. The band may be configured to encircle a plurality or a cluster of papillary muscles, thereby pulling the papillary muscles toward each other with no portion of the band being interposed between the papillary muscles (an example of which is shown in FIG. 3).

According to another embodiment of the present disclosure, a cardiac implant is provided. The cardiac implant may comprise a papillary band having a first end and a second end and being selectively configurable between an elongated configuration where the first end is disconnected from the second end, and a looped configuration where the band is formed into a loop. The cardiac implant may further comprise a clasp attached to the band, closer to the first end of the band than to the second end of the band. The implant may further comprise an elongated insertion cable removably connected to the second end of the band. The papillary band may be configured to form a loop simultaneously encircling a group of papillary muscles, and the elongated insertion cable may be configured to adjust the size of the loop. The band may be configured to contact non-opposed portions of the papillary muscles. The band may be configured to encircle a plurality of papillary muscles, thereby pulling the plurality of papillary muscles toward each other with no portion of the band being interposed between the papillary muscles. In some embodiments, the clasp may be selectively configurable between two configurations—an open configuration and a closed configuration. In the open configuration, the insertion cable and the second end of the band may pass through the clasp. In the closed configuration, the region of the band which passes through the clasp may be held in place so that the band cannot move with respect to the clasp.

Figure 12:
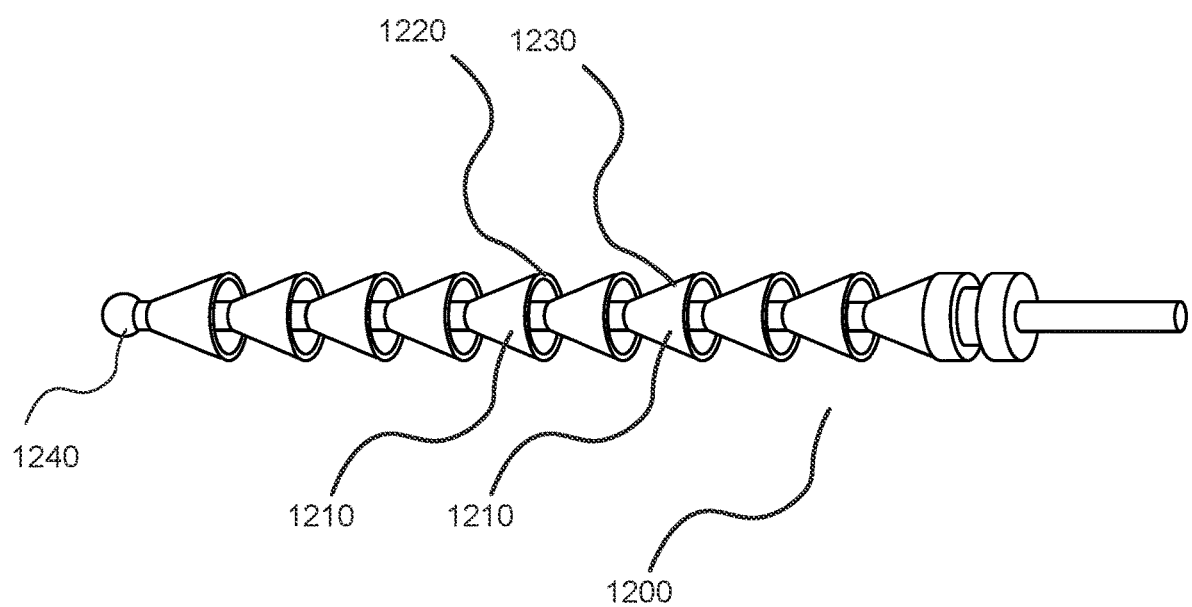
FIG. 12 illustrates an exemplary embodiment of a plurality of sequential locking segments, in accordance with the embodiments of the present disclosure.

According to another embodiment of the present disclosure, a band may comprise a sling including an actuatable clasp and a plurality of sequential locking segments configured to slide into the actuatable clasp. For example, as shown in FIG. 12, a band may comprise a sling 1200 and a plurality of sequential locking segments 1210. Each locking segment 1210 may comprise a ledged region 1220 and a ramped region 1230. Adjacent locking segments 1210 may be configured to flex relative to each other to thereby enable adjacent ramped regions 1230 to cooperate with each other and facilitate a sliding of the locking segments 1210 into an actuatable clasp, such as clasp 240 of FIG. 2 and/or clasp 1140 of FIG. 11.

As shown in FIG. 12, in ramped region 1230, the radius of each locking segment 1210 may increase with increasing distance from one end 1240 of sling 1200. Accordingly, in ramped region 1230, the outer surface of locking segment 1210 may have a positive slope. In contrast, in ledged region 1220, the radius of each locking segment 1210 may decrease with increasing distance from end 1240 of sling 1200. Accordingly, in ledged region 1220, the outer surface of locking segment 1210 may have a negative slope.

In some embodiments, a clasp, such as an actuatable clasp, may lock on the decreased radius of ledged region 1220. As such, the larger positive slope of ramped region 1230 may increase the force necessary to pull sling 1200 into the clasp. Accordingly, the design of locking segments 1210 may need to minimize the positive slope of ramped region 1230 while maintaining sufficient ledge, onto which the clasp can lock.

Figure 13A:
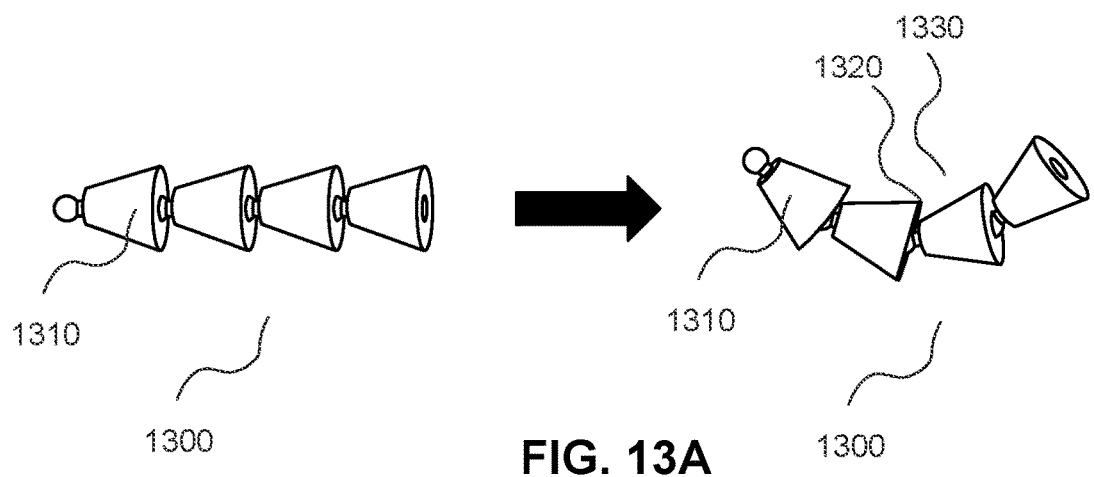
FIG. 13A illustrates an exemplary embodiment of a cooperation of adjacent locking segments when a sling is flexed, in accordance with the embodiments of the present disclosure.
Figure 13B:
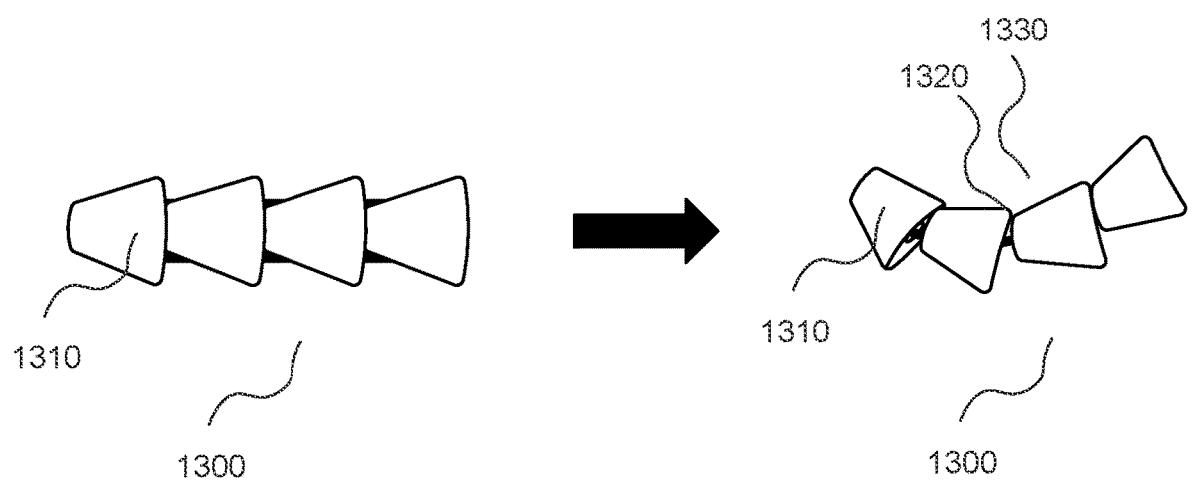
FIG. 13B illustrates another exemplary embodiment of a cooperation of adjacent locking segments when a sling is flexed, in accordance with the embodiments of the present disclosure.

In some embodiments of the present disclosure, a cooperation of adjacent locking segments when a sling is flexed may reduce a magnitude of ledges along an inner side of the flexed sling, thereby reducing the ledge effect. For example, as shown in FIGS. 13A and 13B, when sling 1300 is flexed, adjacent locking segments 1310 cooperate with each other and, thus, magnitudes of ledges 1320 are reduced along an inner side 1330 of the flexed sling 1300. Accordingly, when sling 1300 is flexed and magnitudes of ledges 1320 are reduced, sling 1300 may be able to slide through a clasp more easily.

Figure 14:
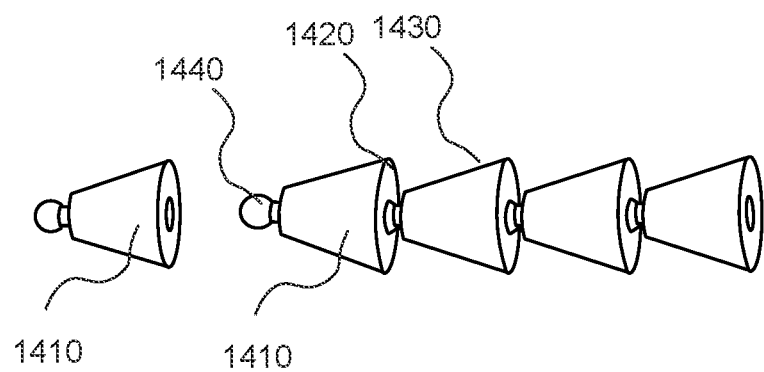
FIG. 14 illustrates an exemplary embodiment of a plurality of locking segments with ball-in-socket joints, in accordance with the embodiments of the present disclosure.

According to some embodiments of the present disclosure, the locking segments may be cone-shaped. For example, as shown in FIG. 14, locking segments 1410 may be cone-shaped and, thus, ledged regions 1420 and ramped regions 1430 may be formed by the cone-shaped segments 1410. Additionally or alternatively, the plurality of locking segments 1410 may comprise individual locking parts that are configured to fit together in a way that allows locking segments 1410 to flex relative to each other. For example, the plurality of locking segments 1410 may fit together with a ball-in-socket joint 1440, a cylinder-in-socket joint, or any other similar type of joint that is capable of locking adjacent segments together while allowing the segments to rotate relative to each other in at least one plane.

Figure 15:
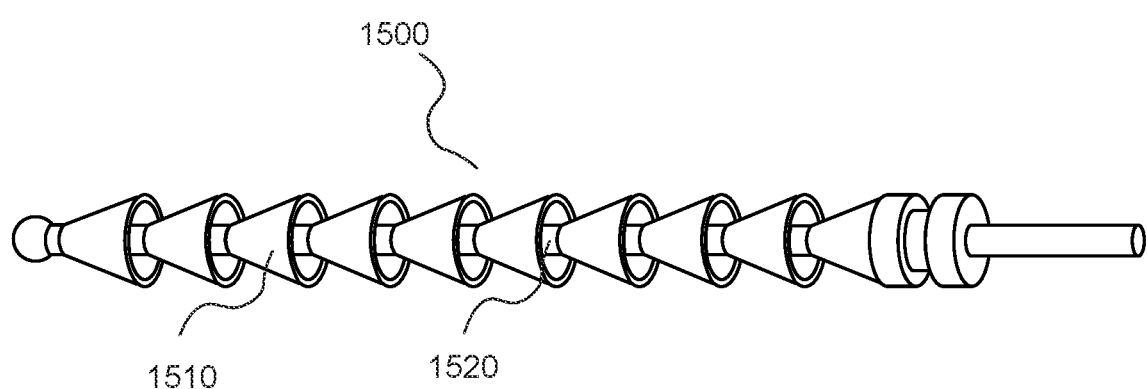
FIG. 15 illustrates exemplary embodiment of a plurality of locking segments with spacers strung on a wire, in accordance with the embodiments of the present disclosure.

In some embodiments, the plurality of locking segments may be strung onto a band, a sling, a wire, a thread, a string, a cable, or the like. Optionally, spacers may be located between each locking segment. For example, as shown in FIG. 15, a sling 1500 contains a plurality of locking segments 1510 strung onto a wire with spacers 1520 between locking segments 1510. The plurality of sequential locking segments 1510 may be individually coupled to the wire so that they cannot move along the wire. In some embodiments, spacers 1520 may be strung onto the wire between adjacent locking segments 1510. In some embodiments, spacers 1520 may be strung between some adjacent locking segments 1510, but not between every adjacent locking segment 1510. In some embodiments, the spacers 1520 may be coupled to the wire and hold the locking segments 1510 in place. Additionally or alternatively, only the first and last of the plurality of locking segments 1510 may be coupled to the wire onto which they are strung. Accordingly, the first and last of the plurality of locking segments 1510 may be configured to hold the remaining locking segments 1510 in place. In yet another embodiment, the plurality of sequential locking segments 1510 may not be coupled to the wire. Rather, other components may be coupled to the wire at the ends of the plurality of locking segments 1510 and the components may be configured to keep the locking segments 1510 in place.

According to some embodiments of the present disclosure, the plurality of sequential locking segments may be integrally formed as a single piece. The single piece may comprise regions that are more flexible than the locking segments. The more flexible regions may connect the less flexible locking segments. In some embodiments, the more flexible regions connecting the locking segments may be made of a material that is different from the material that is used to make the less flexible locking segments. Accordingly, different flexibilities of different regions may result from the use of different materials with different mechanical properties. Additionally or alternatively, the entire chain of sequential locking segments, including the flexible regions and the locking segments, may be made of the same material. Accordingly, different flexibilities of different regions may result from different thicknesses of the same material. For example, the more flexible regions may comprise a first thickness of a material, and the locking segments may comprise a second thickness of the same material. The second thickness may be greater than the first thickness. That is, the locking segments may be thicker than the flexible connecting regions.

Figure 16A:
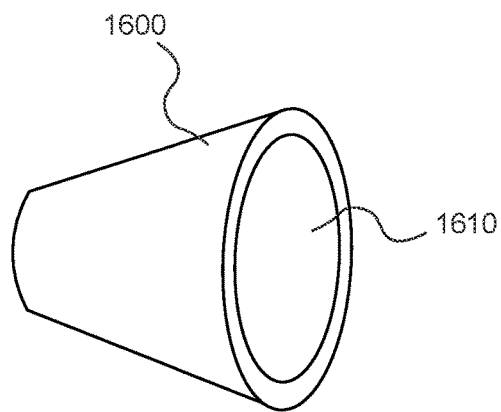
FIG. 16A illustrates an exemplary embodiment of a hollow locking segment, in accordance with the embodiments of the present disclosure.
Figure 16B:
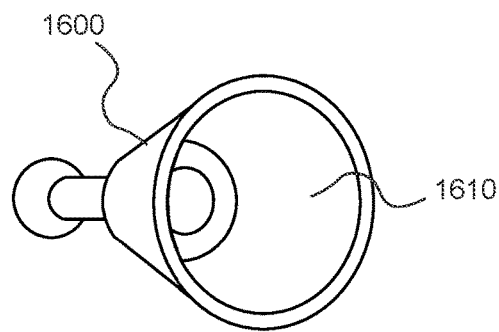
FIG. 16B illustrates an exemplary embodiment of a hollow locking segment with a ball-in-socket joint, in accordance with the embodiments of the present disclosure.
Figure 16C:
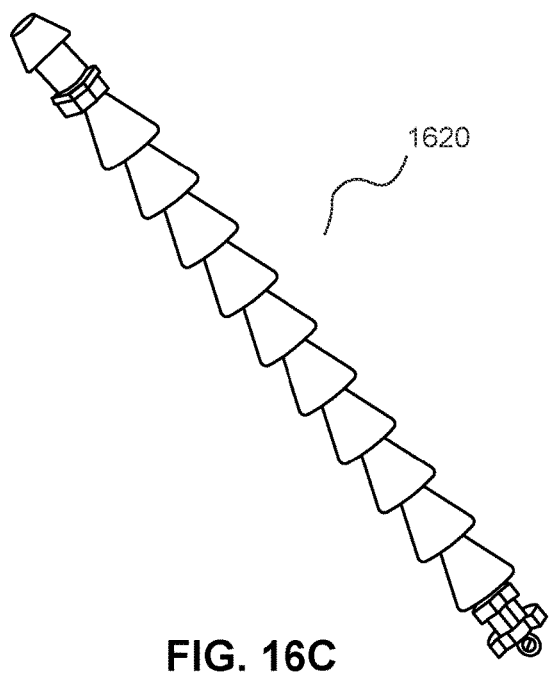
FIG. 16C illustrates an exemplary embodiment of a plurality of the hollow locking segments of FIG. 16A, in accordance with the embodiments of the present disclosure.
Figure 16D:
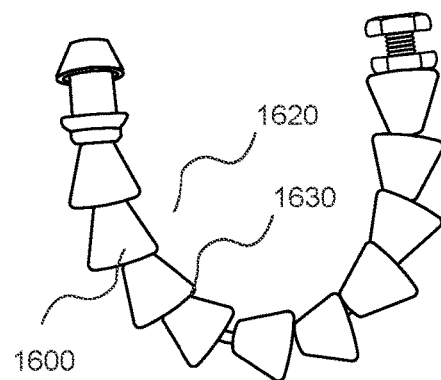
FIG. 16D illustrates another exemplary embodiment of the plurality of hollow locking segments of FIG. 16C when a sling is flexed, in accordance with the embodiments of the present disclosure.

In some embodiments, the ramped region of the locking segments may comprise a hollowed interior. For example, as shown in FIGS. 16A and 16B, locking segments 1600 may comprise a hollowed interior 1610, such as an undercut. The hollowed interior 1610 may allow each locking segments 1600 to rotate relative to a centerline of a chain of sequential locking segments 1600. Accordingly, the magnitude of the ledge on an inner side of a flexed sling may be reduced. For example, as discussed with respect to FIGS. 13A and 13B, when a sling of a plurality of locking segments is flexed, adjacent locking segments may cooperate with each other and, thus, magnitudes of ledges may be reduced along an inner side of the flexed sling. Accordingly, the sling may be able to slide through a clasp more easily. Similarly, FIG. 16C illustrates a sling 1620 of a plurality of sequential locking segments 1600 that is not yet flexed. In contrast, FIG. 16D illustrates the sling 1620 that is flexed. As shown in FIGS. 16C and 16D, when sling 1620 of locking segments 1600 is flexed, magnitudes of ledges 1630 are significantly reduced on an inner side of the flexed sling 1620. The hollowed interior 1610 of each locking segment 1600 may allow adjacent locking segments 1600 to cooperate with each other better when sling 1620 is flexed, and thus, facilitate further reduction of magnitudes of the ledges.

Figure 17:
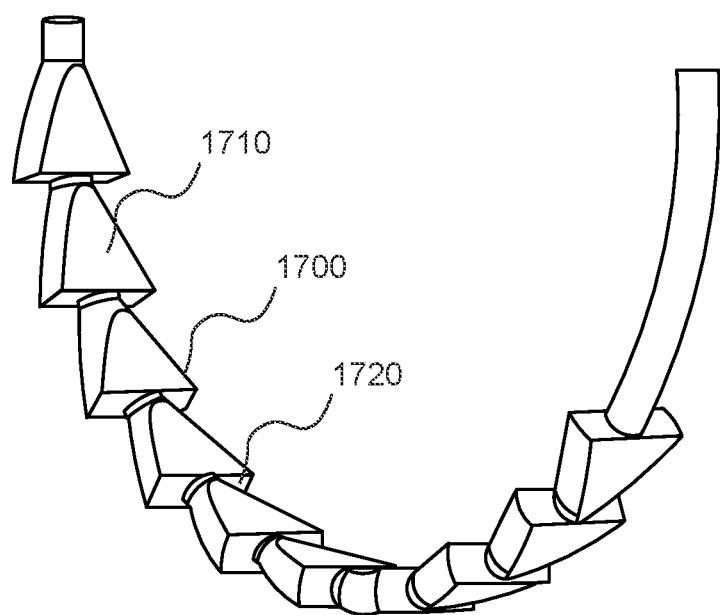
FIG. 17 illustrates another exemplary embodiment of a plurality of sequential locking segments, in accordance with the embodiments of the present disclosure.

In some embodiments of the present disclosure, a ramped region of a locking segment may expand in radius in only one plane or in only one direction. For example, as shown in FIG. 17, a ramped region 1700 of a locking segment 1710 may expand in radius in only one plane. When ramped region 1700 expands in radius in only one plane, the ledge effect may be substantially eliminated entirely, with the exception of some possible variation in force due to non-uniform bending. In addition, when ramped region 1700 expands in radius in only one plane, the locking strength of a clasp may be reduced because the ledges 1720 of each locking segment 1710 expand in only one plane as well within a thickness of each locking segment 1710.

Figure 18:
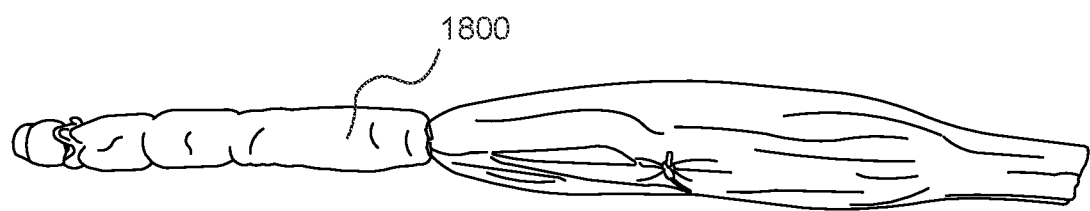
FIG. 18 illustrates an exemplary embodiment of a sling formed of a tube with a plurality of sequential locking segments disposed inside the tube, in accordance with the embodiments of the present disclosure.

In some embodiments of the present disclosure, the band may comprise a tube and a plurality of sequential locking segments may be disposed inside the tube. For example, as seen in FIG. 18, a plurality of sequential locking segments may be disposed inside tube 1800. Tube 1800 may be made of a soft, flexible material such that a clasp can close on an outside surface of tube 1800 and lock firmly onto a ledged region of a locking segment disposed inside tube 1800. In some embodiments, tube 1800 may be made of ePTFE, Dacron, or any other biocompatible material that is soft and flexible. In some embodiments, one end of tube 1800 may be connected to one end of a chain of sequential locking segments. In other embodiments, one end of tube 1800 may be connected to one end of the chain of sequential locking segments through an adapter. For example, an adapter may be connected to an end of the chain of sequential locking segments and an end of tube 1800, and thus, connect the chain of sequential locking segments to tube 1800. In yet another embodiment, a location in the middle of tube 1800 may be connected to another end of the chain of sequential locking segments.

Figure 19A:
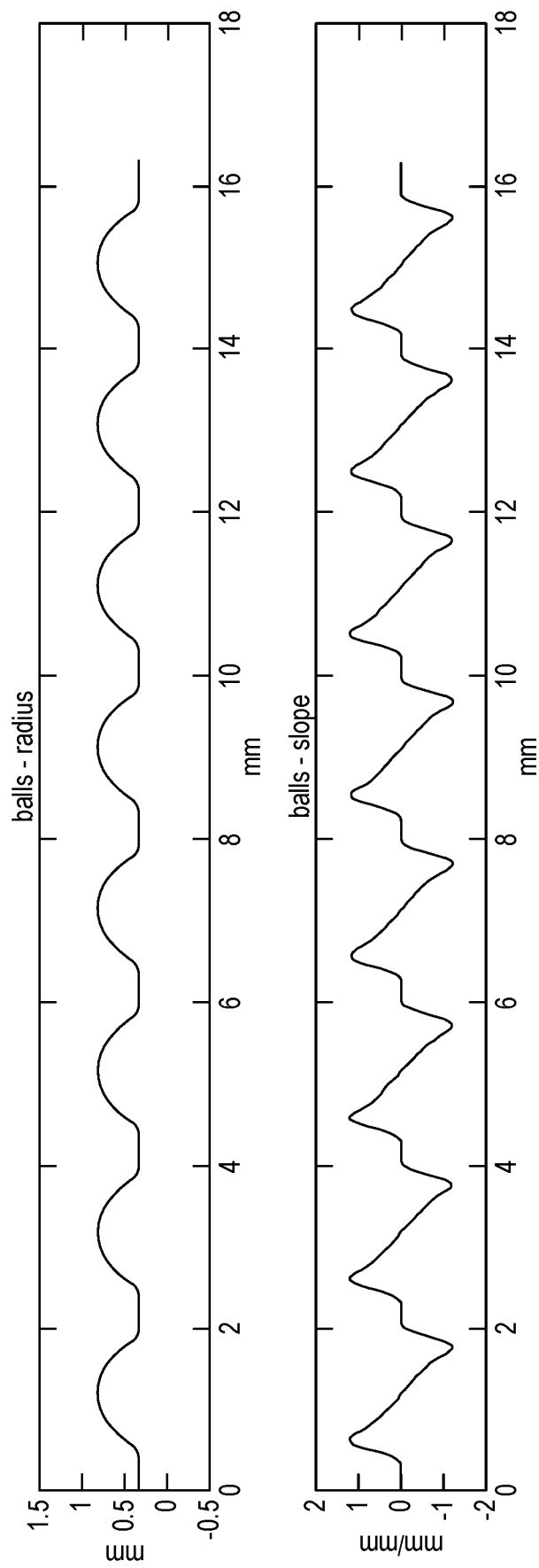
FIG. 19A is a graph illustrating a radius and slope along a length of a flexed chain of ball-shaped sequential locking segments, in accordance with the embodiments of the present disclosure.
Figure 19B:
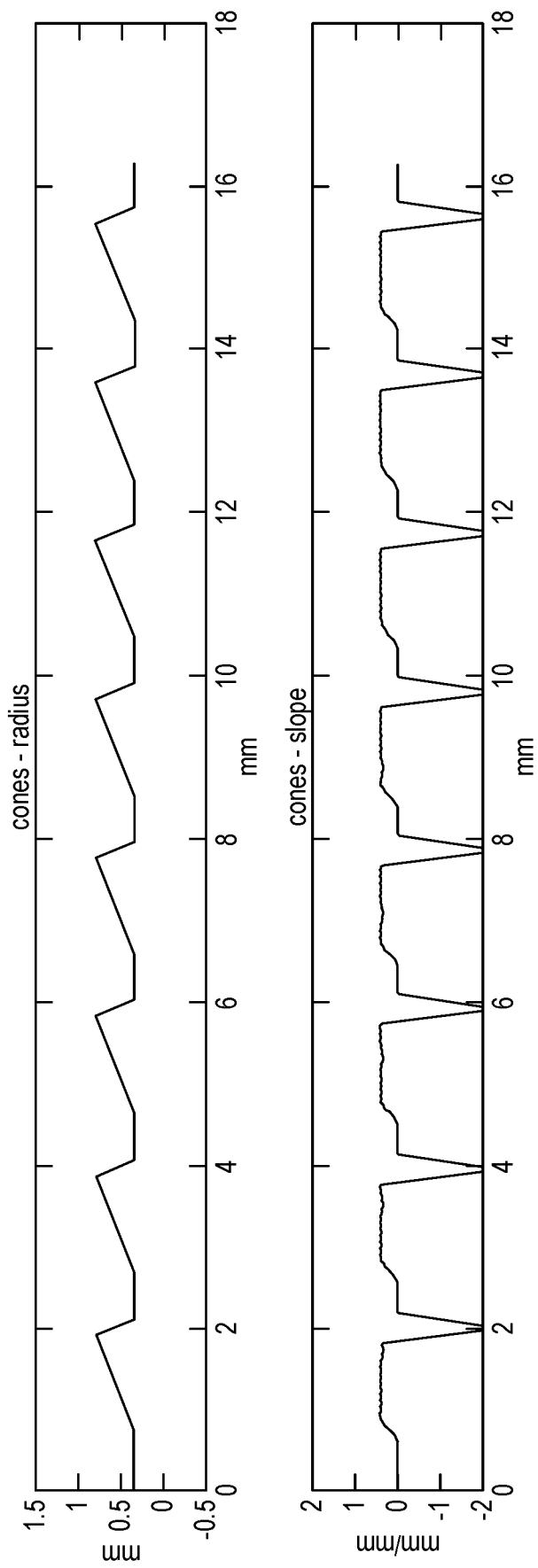
FIG. 19B is a graph illustrating a radius and slope along a length of a flexed chain of cone-shaped sequential locking segments, in accordance with the embodiments of the present disclosure.
Figure 19C:
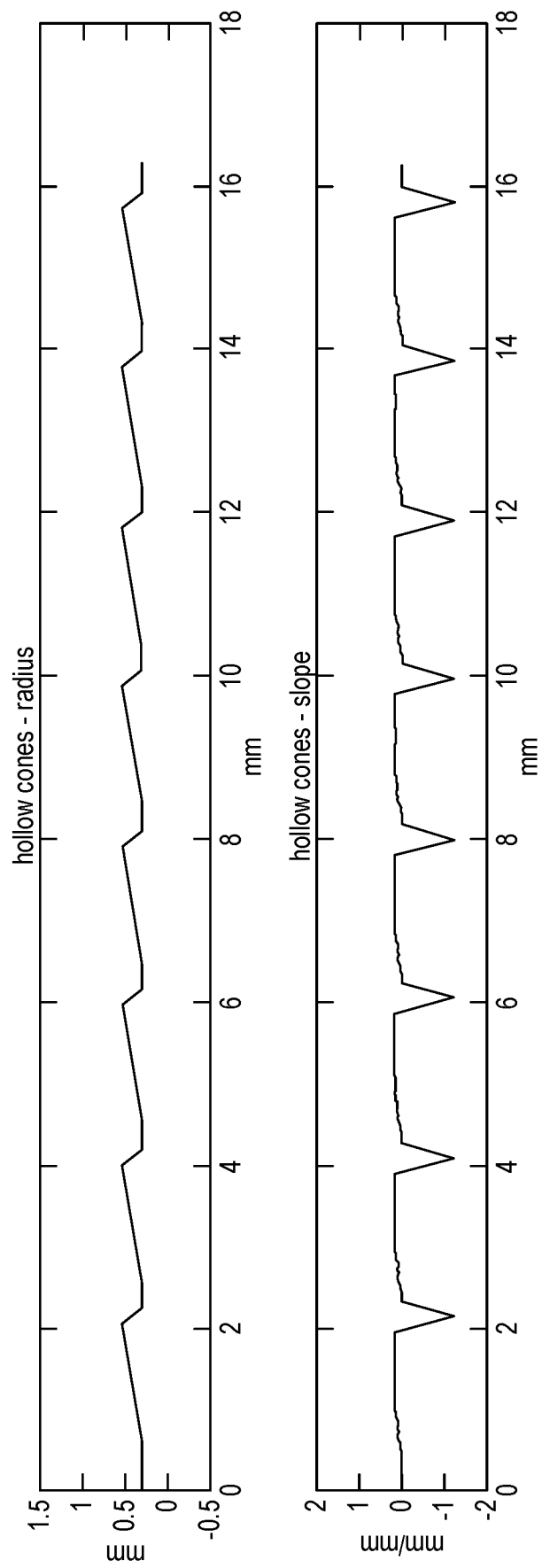
FIG. 19C is a graph illustrating a radius and slope along a length of a flexed chain of hollow cone-shaped sequential locking segments, in accordance with the embodiments of the present disclosure.

FIGS. 19A-19C are graphs illustrating radii and slopes along a length of a flexed chain of ball-shaped sequential locking segments, cone-shaped sequential locking segments, and hollow cone-shaped sequential locking segments, respectively. As shown in FIG. 19A, for example, the top graph illustrates a radius along the length of an inner side of a flexed chain of ball-shaped sequential locking segments. The bottom graph illustrates that the maximum slope along the length of the flexed chain of ball-shaped locking segments is about 1.2 mm/mm. In contrast, FIG. 19B illustrates the radius (top graph) and slope (bottom graph) along a length of a flexed chain of cone-shaped sequential locking segments. Compared to the maximum slope along a length of a flexed chain of ball-shaped locking segments, the maximum slope along a length of a flexed chain of cone-shaped locking segments is reduced to about 0.4 mm/mm. Accordingly, cone-shaped locking segments may provide an improvement over ball-shaped locking segments by reducing the maximum slope from about 1.2 mm/mm to about 0.4 mm/mm.

Similarly, FIG. 19C illustrates the radius (top graph) and slope (bottom graph) along a length of a flexed chain of hollow cone-shaped sequential locking segments. Compared to the maximum slope along a length of a flexed chain of ball-shaped locking segments and along a length of a flexed chain of cone-shaped locking segments, the maximum slope along a length of a flexed chain of hollow cone-shaped locking segments is further reduced to about 0.17 mm/mm. Accordingly, hollow cone-shaped locking segments may reduce the maximum slope to about 0.17 mm/mm, which is lower than both ball-shaped locking segments and cone-shaped locking segments. The hollow cone-shaped locking segments may also differ in that the hollow cone-shaped segments may have a comparatively reduced radius, which may reduce the force necessary to pull the chain of locking segments into a clasp, especially in the case of increasing tension as the sling is tightened.

Figure 20A:
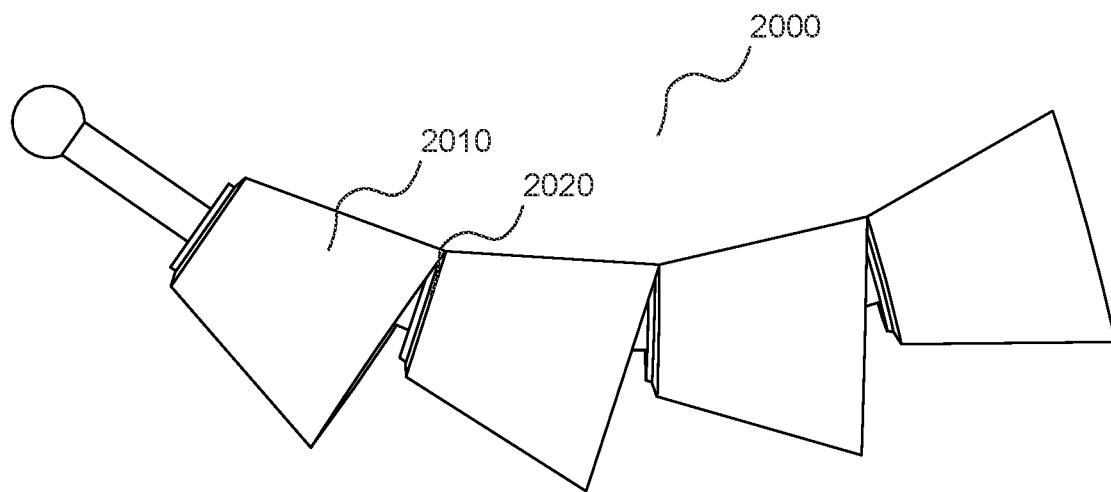
FIG. 20A illustrates an exemplary embodiment of hollow cone-shaped locking segments with an indentation, in accordance with the embodiments of the present disclosure.
Figure 20B:
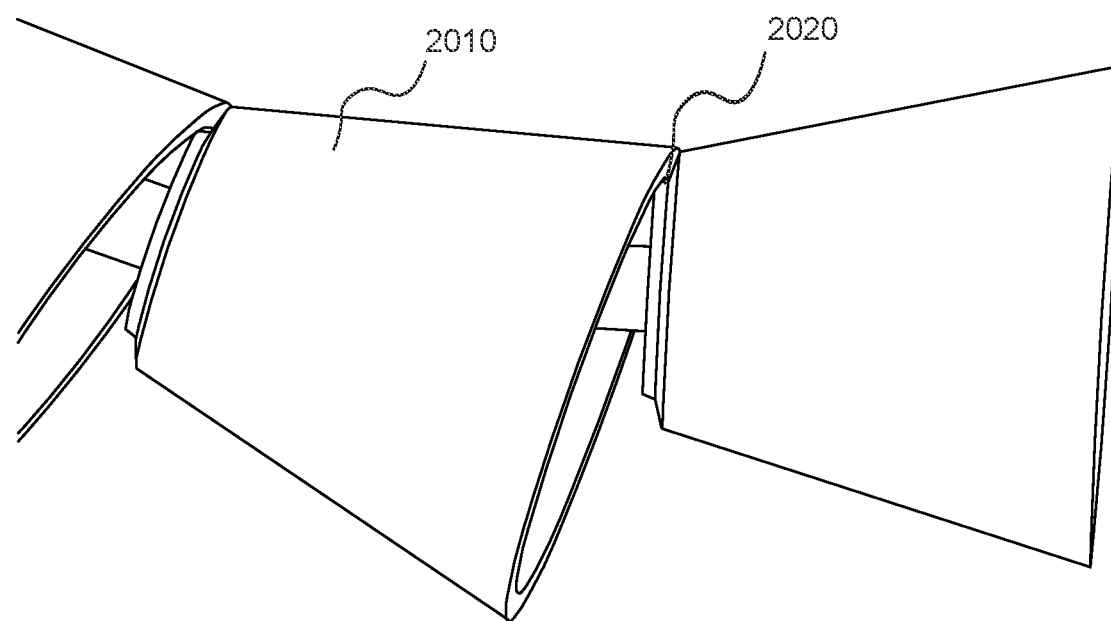
FIG. 20B another view of the hollow cone-shaped locking segments of FIG. 20A, in accordance with the embodiments of the present disclosure.

According to another embodiment of the present disclosure, hollow cone-shaped locking segments may comprise indentations. For example, as shown in FIGS. 20A and 20B, hollow cone-shaped locking segments 2010 may comprise indentations 2020. Hollow cone-shaped locking segments 2010 may comprise ball-in-socket joints, such as ball-in-socket joints 1440 of FIG. 14. In some embodiments, as seen in FIGS. 20A and 20B, indentations 2020 may allow adjacent locking segments 2010 to align with each other to form a smooth surface with reduced or no ledges along an inner side of sling 2000 when sling 2000 is flexed. Accordingly, when locking segments 2010 are aligned with each other via indentations 2020, the radius from the centerline may be constant with zero positive slope, thereby eliminating or reducing any ledge effect with the exception of possible variation in force due to an angle between adjacent locking segments 2010.

Figure 21:
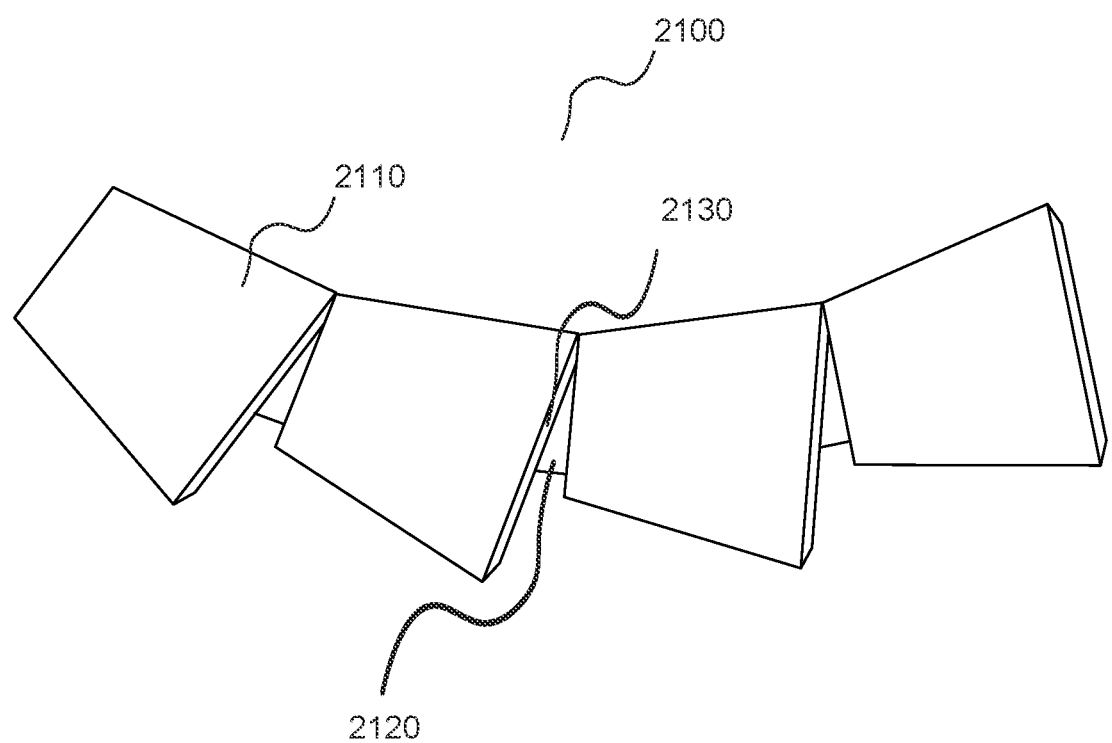
FIG. 21 illustrates an exemplary embodiment of hollow cone-shaped locking segments with spacers, in accordance with the embodiments of the present disclosure.

In some embodiments, hollow cone-shaped locking segments may be strung on a band, a sling, a wire, a thread, a string, a cable, or the like with spacers between each locking segment. For example, as shown in FIG. 21, hollow cone-shaped locking segments 2110 may be strung on a band 2100 with spacers 2120 between each adjacent locking segment 2110. Similar to the hollow cone-shaped locking segments 2010 of FIGS. 20A and 20B, hollow cone-shaped locking segments 2110 may comprise indentations 2130. Indentations 2130 may allow adjacent locking segments 2110 to align with each other to form a smooth surface with no ledges along an inner side of sling 2100 when sling 2100 is flexed. Accordingly, when locking segments 2110 are aligned with each other via indentations 2130, the radius from the centerline may be constant with zero positive slope, thereby eliminating or significantly reducing a ledge effect with the exception of possible variation in force due to an angle between adjacent locking segments 2110.

According to another embodiment of the present disclosure, an improved method of visualizing devices is disclosed. For example, manipulation and actuation of transcatheter devices within a body is generally guided by visualization using fluoroscopy. Accordingly, in order to aid in the visualization of transcatheter devices using fluoroscopy, radiopaque markers may be used. Radiopaque markers may appear with high contrast on fluoroscopic images and may be attached to transcatheter devices at critical locations such that the position, orientation, and/or relative positions of the transcatheter devices can be clearly visualized.

In some embodiments, radiopaque markers may be disposed at one or more locations on a component of a band, on the band, or on a band delivery device. The radiopaque markers may aid in the positioning and deployment of, for example, a transcatheter papillary muscle band or a ventricular band. In some embodiments of the present disclosure, radiopaque markers may aid in the positioning of a transcatheter band by providing visual confirmation that the band is properly positioned for deployment. For example, for a band including a clasp, such as an actuatable clasp, at a first end thereof that locks onto a position along the band in order to form a loop, visual confirmation that a second end of the band has been inserted far enough into the clasp may be needed. Accordingly, accidental actuation of the clasp before sufficient insertion of the second end of the band into the clasp can be avoided.

In another embodiment, radiopaque markers may aid in the deployment of a transcatheter band by providing a visual confirmation that clasp actuation has occurred. For example, for a band that comprises a clasp that is actuated by the retraction of a clasp retainer, visual confirmation that the clasp retainer has actually retracted from the clasp may be needed in order to provide confidence to the user that the clasp has been actuated and is locked in place.

In yet another embodiment of the present disclosure, a band delivery device may comprise a radiopaque marker at a distal end thereof. The radiopaque marker may be adjacent to a clasp disposed in the band, and the band may comprise another radiopaque marker at a second end thereof. Accordingly, when the radiopaque marker on the second end of the band passes the radiopaque marker on the distal end of the band delivery device, this may provide confirmation that the second end of the band is sufficiently inserted through the clasp that the clasp can be actuated.

In some embodiments of the present disclosure, the band delivery device may comprise a radiopaque marker at a distal end thereof, adjacent to the clasp of the band, and the band insertion cable, which may be attached to the second end of the band, may comprise a radiopaque marker near a position at which the insertion cable attaches to the band. Accordingly, when the radiopaque marker on the insertion cable passes the radiopaque marker on the distal end of the delivery device, this provides confirmation that the second end of the band is sufficiently inserted through the clasp that the clasp can be actuated.

In some embodiments of the present disclosure, the delivery device may comprise a radiopaque marker on a clasp retainer, and the band may comprise a radiopaque marker at a second end thereof. Accordingly, when the radiopaque marker on the second end of the band passes the radiopaque marker on the clasp retainer, this provides confirmation that the second end of the band is sufficiently inserted through the clasp that the clasp can be actuated.

In some embodiments of the present disclosure, the band delivery device may comprise a radiopaque marker on the clasp retainer, and the band insertion cable, which may be attached to the second end of the band, may comprise a radiopaque marker near a position at which the insertion cable attaches to the band. Accordingly, when the radiopaque marker on the insertion cable passes the radiopaque marker on the clasp retainer, this provides confirmation that the second end of the band is sufficiently inserted through the clasp that the clasp can be actuated.

In some embodiments of the present disclosure, the band delivery device may comprise a radiopaque marker on the clasp retainer and a second radiopaque marker on the distal end of the delivery device. Additionally or alternatively, the radiopaque markers may be aligned such that, when the retainer is within the clasp, the radiopaque markers appear in the fluoroscopic images to be a single marker (e.g., overlapping each other). In addition, when the retainer is retracted from the clasp, the markers appear as two separate markers in the fluoroscopic images (e.g., no longer overlapping each other). Additionally or alternatively, the radiopaque markers may be aligned such that, when the retainer is within the clasp, the radiopaque markers appear in the fluoroscopic images as two separate markers in the fluoroscopic images, and when the retainer is retracted from the clasp the markers overlap each other and appear as a single marker in the fluoroscopic images. In some embodiments, the radiopaque markers may comprise cylindrical bands.

Figure 22A:
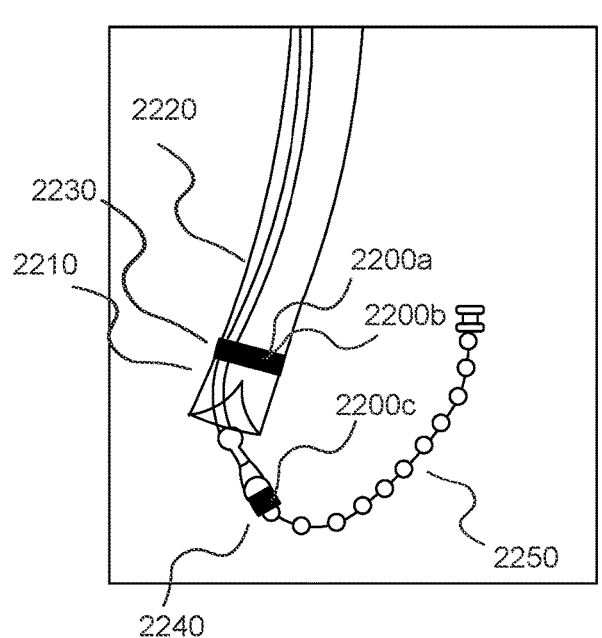
FIG. 22A illustrates an exemplary embodiment of radiopaque markers on a distal end of a delivery device, a clasp retainer, and a second end of a sling, in accordance with the embodiments of the present disclosure.

Referring to FIGS. 22A-22D, for example, radiopaque markers may be disposed on a delivery device, on a clasp retainer, and on a band in order to confirm clasp actuation. For example, as shown in FIG. 22A, a radiopaque marker 2200*a* may be disposed on a distal end 2210 of a delivery device 2220, a radiopaque marker 2200*b* may be disposed on a clasp retainer 2230, and a radiopaque marker 2200*c* may be disposed on a second end 2240 of a band 2250. In FIG. 22A, radiopaque markers 2200*a* and 2200*b* appear as a single band in the fluoroscopic image, thereby suggesting that radiopaque markers 2200*a* and 2200*b* are aligned and overlapping each other. In the fluoroscopic image of FIG. 22A, radiopaque marker 2200*c* on second end 2240 of band 2250 is located outside of distal end 2210 of delivery device 2220, and thus, second end 2240 of band 2250 has not yet passed through a clasp associated with clasp retainer 2230.

Figure 22B:
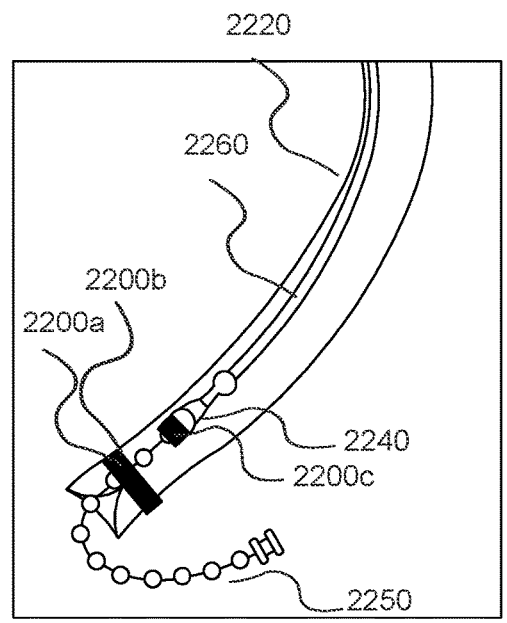
FIG. 22B illustrates another exemplary embodiment of the radiopaque markers of FIG. 22A, in accordance with the embodiments of the present disclosure.
Figure 22C:
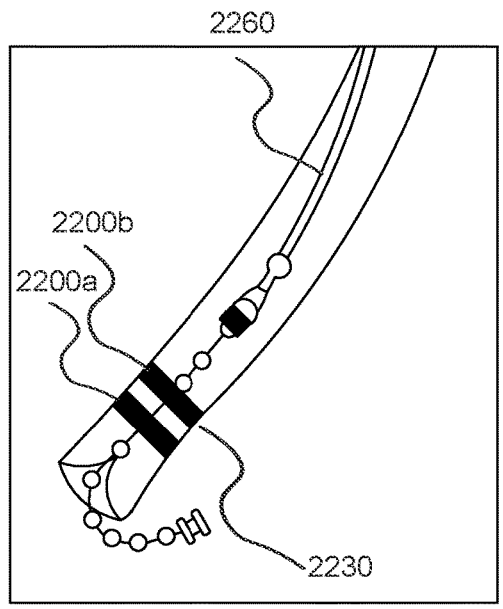
FIG. 22C illustrates another exemplary embodiment of the radiopaque markers of FIG. 22A, in accordance with the embodiments of the present disclosure.
Figure 22D:
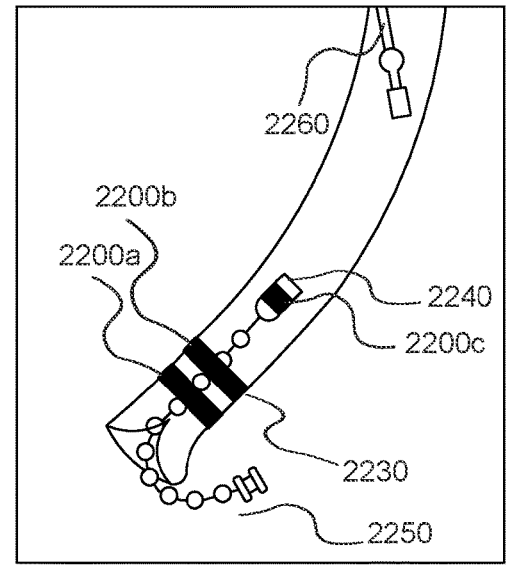
FIG. 22D illustrates another exemplary embodiment of the radiopaque markers of FIG. 22A, in accordance with the embodiments of the present disclosure.

Referring now to FIG. 22B, radiopaque marker 2200*c* has passed through radiopaque marker 2200*a* of delivery device 2220 and is located inside delivery device 2220. This indicates that second end 2240 of band 2250 has been inserted through the clasp and that the clasp may be actuated. Referring now to the fluoroscopic image of FIG. 22C, radiopaque markers 2200*a* and 2200*b* appear separated and are no longer overlapping each other. This confirms that that the clasp associated with clasp retainer 2230 has been actuated, and thus, locked onto a portion of band 2250. As seen in FIG. 22D, even when a band insertion cable 2260 is detached from band 2250, radiopaque marker 2200*c* remains on second end 2240 of band 2250.

Figure 23A:
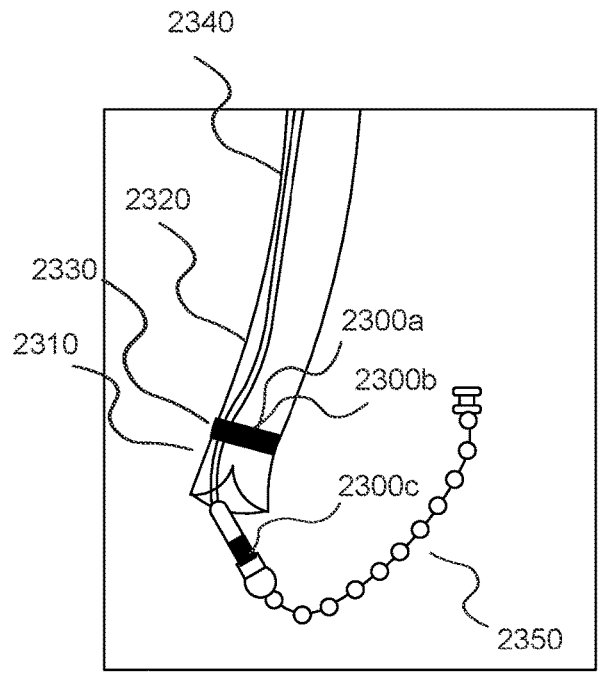
FIG. 23A illustrates an exemplary embodiment of radiopaque markers on a distal end of a delivery device, a clasp retainer, and a sling insertion cable, in accordance with the embodiments of the present disclosure.

Referring now to FIGS. 23A-23D, in some embodiments, radiopaque markers may be disposed on a delivery device, on a clasp retainer, and on a band insertion cable in order to confirm clasp actuation. For example, as shown in FIG. 23A, a radiopaque marker 2300*a* may be disposed on a distal end 2310 of a delivery device 2320, a radiopaque marker 2300*b* may be disposed on a clasp retainer 2330, and a radiopaque marker 2300*c* may be disposed on a band insertion cable 2340. In FIG. 23A, radiopaque markers 2300*a* and 2300*b* appear as a single band in the fluoroscopic image, thereby suggesting that radiopaque markers 2300*a* and 2300*b* are aligned and overlapping each other. In the fluoroscopic image of FIG. 23A, radiopaque marker 2300*c* on band insertion cable 2340 is located outside of distal end 2310 of delivery device 2320, thereby indicating that an end of a band 2350 attached to band insertion cable 2340 has not yet passed through a clasp associated with clasp retainer 2330.

Figure 23B:
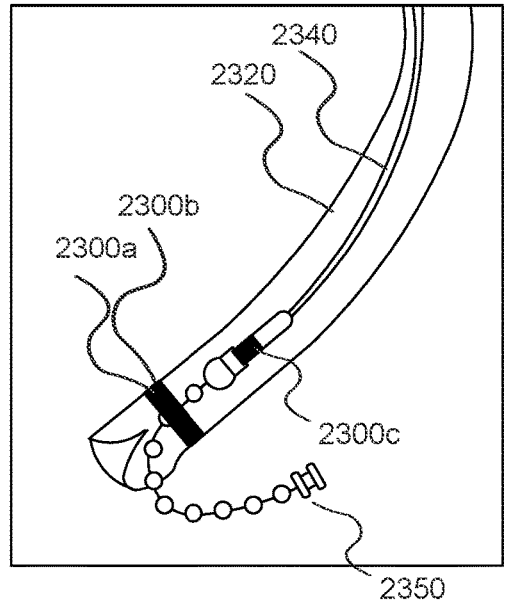
FIG. 23B illustrates another exemplary embodiment of the radiopaque markers of FIG. 23A, in accordance with the embodiments of the present disclosure.
Figure 23C:
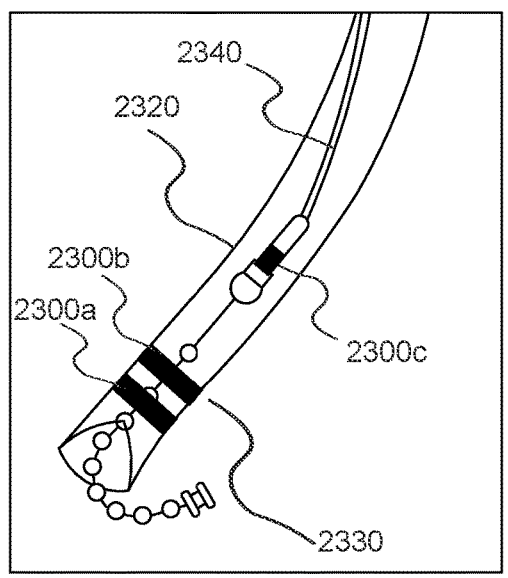
FIG. 23C illustrates another exemplary embodiment of the radiopaque markers of FIG. 23A, in accordance with the embodiments of the present disclosure.
Figure 23D:
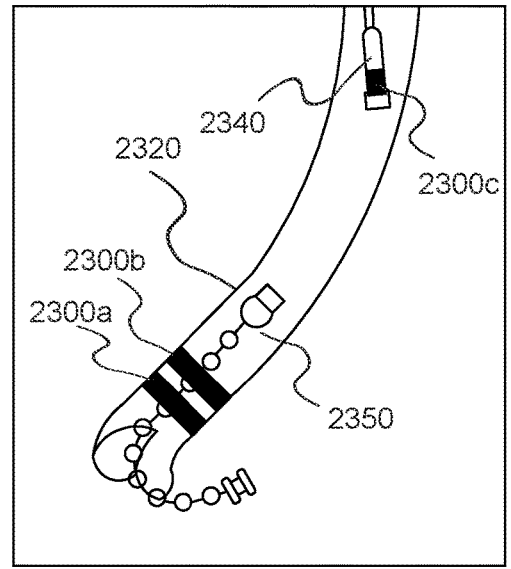
FIG. 23D illustrates another exemplary embodiment of the radiopaque markers of FIG. 23A, in accordance with the embodiments of the present disclosure.

Referring now to FIG. 23B, radiopaque marker 2300*c* has passed through radiopaque marker 2300*a* of delivery device 2320 and is located inside delivery device 2320. This indicates that the end of band 2350 attached to band insertion cable 2340 has been inserted through the clasp and that the clasp may be actuated. Referring now to the fluoroscopic image of FIG. 23C, radiopaque markers 2300*a* and 2300*b* appear separated and are no longer overlapping each other. This confirms that the clasp associated with clasp retainer 2330 has been actuated, and thus, locked onto a portion of band 2350. As seen in FIG. 23D, radiopaque marker 2300*c* is detached from the end of band 2350, indicating that band insertion cable 2340 has been detached from the end of band 2350.

While the present disclosure is described herein with reference to illustrative embodiments of catheters, bands, and guidewires used for particular applications, such as for papillary muscle repositioning and improving cardiac function, it should be understood that the embodiments described herein are not limited thereto. Those having ordinary skill in the art and access to the teachings provided herein will recognize additional modifications, applications, embodiments, and substitution of equivalents that all fall within the scope of the disclosed embodiments. Accordingly, the disclosed embodiments are not to be considered as limited by the foregoing or following descriptions.

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description.

What is claimed is:

1. A cardiac device, comprising:
a band configured to form a loop within a heart, the band including a first end and a second end; and
an actuatable clasp associated with the first end of the band, the actuatable clasp being configured to transition upon actuation from an open configuration to a closed configuration and form the band into a fixed length loop after the second end passes through the actuatable clasp,
wherein the actuatable clasp is configured for actuation via a catheter, and
wherein the actuatable clasp is configured to be mechanically locked to a distal end of a delivery device when the actuatable clasp is in the open configuration and configured to be disconnected from the delivery device upon transitioning to the closed configuration.

2. The cardiac device of claim 1, wherein the actuatable clasp includes a cylinder with a plurality of flaps protruding from one end of the cylinder.

3. The cardiac device of claim 2, wherein, in the closed configuration, the plurality of flaps are bent inward toward a center of the cylinder to form the actuatable clasp configured to grasp a portion of the band that passes through the actuatable clasp.

4. The cardiac device of claim 2, wherein the plurality of flaps include pointed tips configured to hold or puncture the band when the actuatable claps is in the closed configuration.

5. The cardiac device of claim 2, wherein the plurality of flaps include flat or rounded tips configured to fit between one or more protrusions on the band to prevent the one or more protrusions from passing through the actuatable clasp when the actuatable clasp is in the closed configuration.

6. The cardiac device of claim 2, wherein the plurality of flaps are biased towards the closed configuration and configured to be elastically bent into the open configuration to adjust the band.

7. The cardiac device of claim 6, wherein the plurality of flaps are configured to return to the closed configuration upon actuation of the actuatable clasp by a clasp actuator.

8. The cardiac device of claim 1, wherein the second end of the band includes one or more protrusions, and wherein the actuatable clasp is configured to close between the one or more protrusions in the closed configuration.

9. The cardiac device of claim 8, wherein the one or more protrusions include at least one of one or more objects, one or more balls, or one or more spikes.

10. The cardiac device of claim 9, wherein the one or more protrusions include one or more balls, and wherein the one or more balls are made of at least one of plastic, metal, or polymer.

11. The cardiac device of claim 8, wherein the one or more protrusions are configured to pass through the actuatable clasp in a first direction, and wherein the actuatable clasp is configured to prevent the one or more protrusions from passing through the actuatable clasp in a second direction opposite the first direction when the actuatable clasp is in the closed configuration.

12. The cardiac device of claim 1, wherein the actuatable clasp includes a cylinder with one or more cuts in a wall of the cylinder.

13. The cardiac device of claim 12, further comprising a wire or a ring disposed around the first end of the band over the one or more cuts, the wire or the ring configured to push a material of the band into the one or more cuts in the wall of the cylinder.

14. The cardiac device of claim 1, wherein an inner diameter and an outer diameter of a distal end of the delivery device is similar to an inner diameter and outer diameter of the actuatable clasp.

15. The cardiac device of claim 14, wherein the distal end of the delivery device is cut with a pattern, and wherein the pattern is complementary to a shape of the plurality of flaps of the actuatable clasp such that when the actuatable clasp is in the open configuration, the plurality of flaps are configured to lock into the cut pattern at the distal end of the delivery device.

16. The cardiac device of claim 15, wherein, when the actuatable clasp is in the closed configuration, the plurality of flaps are configured to disconnect from the cut pattern at the distal end of the delivery device.

17. The cardiac device of claim 16, wherein upon transitioning from the open configuration to the closed configuration, the actuatable clasp is configured to both lock the band into a loop by grasping the second end of the band and disconnect from the cut pattern at the distal end of the delivery device.

18. The cardiac device of claim 1, further comprising a clasp actuator configured to actuate the actuatable clasp, wherein the actuatable clasp is configured to transition from the open configuration to the closed configuration upon actuation by the clasp actuator.

19. The cardiac device of claim 18, further comprising a clasp retainer ring disposed within the actuatable clasp and a pull-wire coupled to the clasp retainer ring.

20. The cardiac device of claim 19, wherein the clasp retainer ring is configured to retract from the actuatable clasp upon actuation of the actuatable clasp by the clasp actuator.

\* \* \* \* \*